(12) United States Patent
Abrams et al.

(10) Patent No.: US 7,141,055 B2
(45) Date of Patent: Nov. 28, 2006

(54) RESECTION AND ANASTOMOSIS DEVICES AND METHODS

(75) Inventors: Jerome H. Abrams, St. Paul, MN (US); Claire T. Hovland, Andover, MN (US); Paul J. Robinson, Andover, MN (US)

(73) Assignee: Surgical Connections, Inc., Andover, MN (US)

( * ) Notice: Subject to any disclaimer, the term of this patent is extended or adjusted under 35 U.S.C. 154(b) by 353 days.

(21) Appl. No.: 10/422,598

(22) Filed: Apr. 24, 2003

(65) Prior Publication Data

US 2004/0092960 A1    May 13, 2004

Related U.S. Application Data

(60) Provisional application No. 60/375,148, filed on Apr. 24, 2002.

(51) Int. Cl.
*A61B 17/24* (2006.01)
(52) U.S. Cl. .......... 606/115; 606/110; 606/139; 606/213; 606/219
(58) Field of Classification Search .......... 606/110, 606/115, 139, 213, 219; 600/201–246
See application file for complete search history.

(56) References Cited

U.S. PATENT DOCUMENTS

| | | | |
|---|---|---|---|
| 4,841,888 A * | 6/1989 | Mills et al. ............ | 112/169 |
| 4,960,419 A * | 10/1990 | Rosenberg ............. | 606/45 |
| 5,346,501 A | 9/1994 | Regula et al. | |
| 5,395,030 A | 3/1995 | Kuramoto et al. | |
| 5,776,142 A | 7/1998 | Gunderson | |
| 5,839,639 A | 11/1998 | Sauer et al. | |
| 6,119,913 A | 9/2000 | Adams et al. | |
| 6,126,058 A | 10/2000 | Adams et al. | |
| 6,149,667 A | 11/2000 | Hovland et al. | |
| 6,338,737 B1 | 1/2002 | Toledano | |
| 6,343,731 B1 | 2/2002 | Adams et al. | |
| 6,383,198 B1 * | 5/2002 | Hamilton ............... | 606/115 |
| 6,398,795 B1 * | 6/2002 | McAlister et al. ....... | 606/139 |
| 6,517,566 B1 | 2/2003 | Hovland et al. | |
| 6,605,078 B1 * | 8/2003 | Adams .................. | 606/1 |
| 6,632,227 B1 * | 10/2003 | Adams .................. | 606/110 |
| 6,648,897 B1 * | 11/2003 | Hamilton ............... | 606/115 |
| 2002/0020732 A1 | 2/2002 | Adams et al. | |

FOREIGN PATENT DOCUMENTS

WO    WO 92/17117    10/1992

* cited by examiner

*Primary Examiner*—Michael J. Hayes
*Assistant Examiner*—Michael G. Mendoza
(74) *Attorney, Agent, or Firm*—Dicke, Billig & Czaja PLLC

(57) ABSTRACT

According to embodiments of the invention, an apparatus for moving a diseased portion of an anatomical structure with respect to a healthy portion of an anatomical structure includes a first vacuum section adapted to apply vacuum force to and hold the healthy portion, and a second vacuum section adapted to apply vacuum force to and hold the diseased portion, wherein the second vacuum section is adapted to withdraw within the first vacuum section.

40 Claims, 20 Drawing Sheets

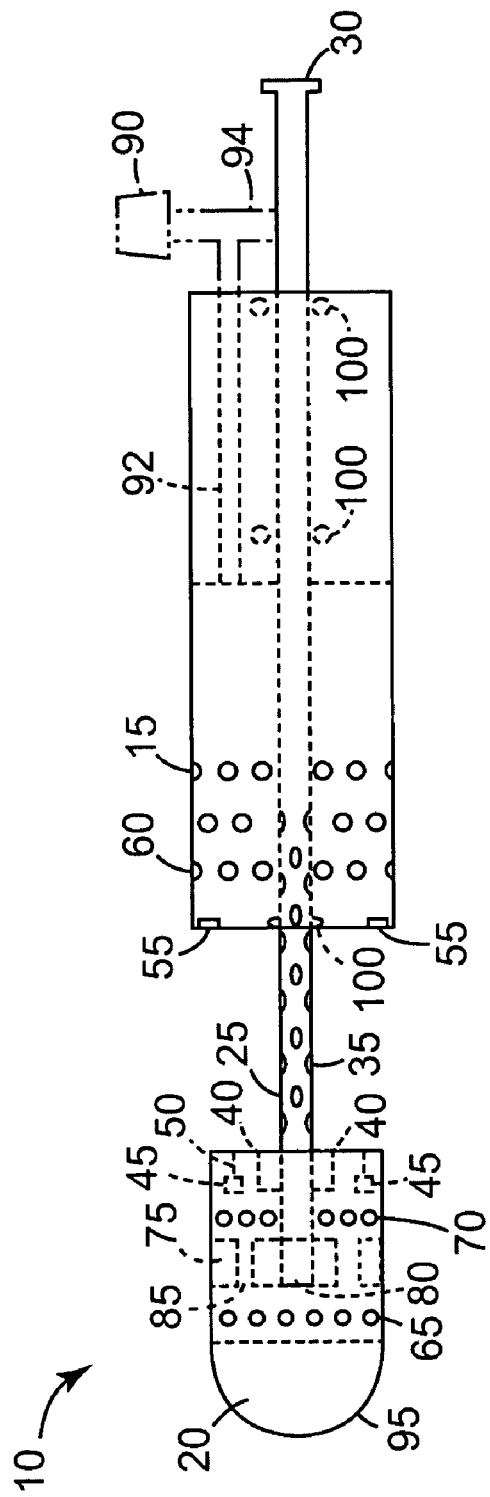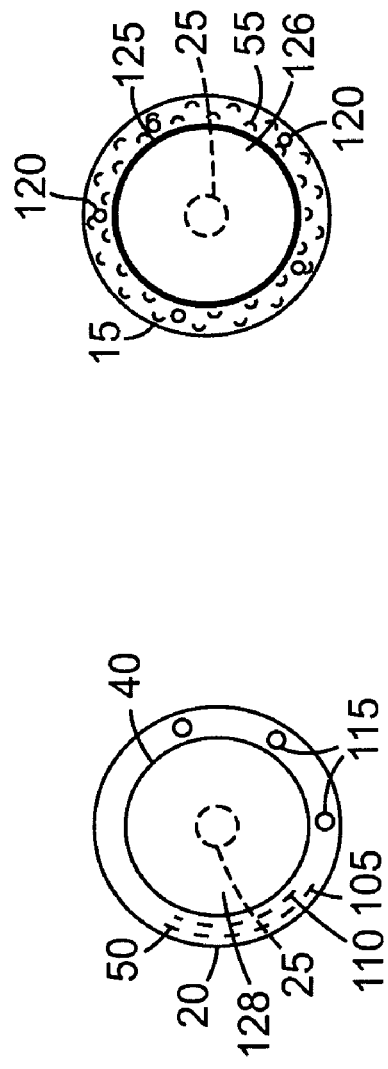

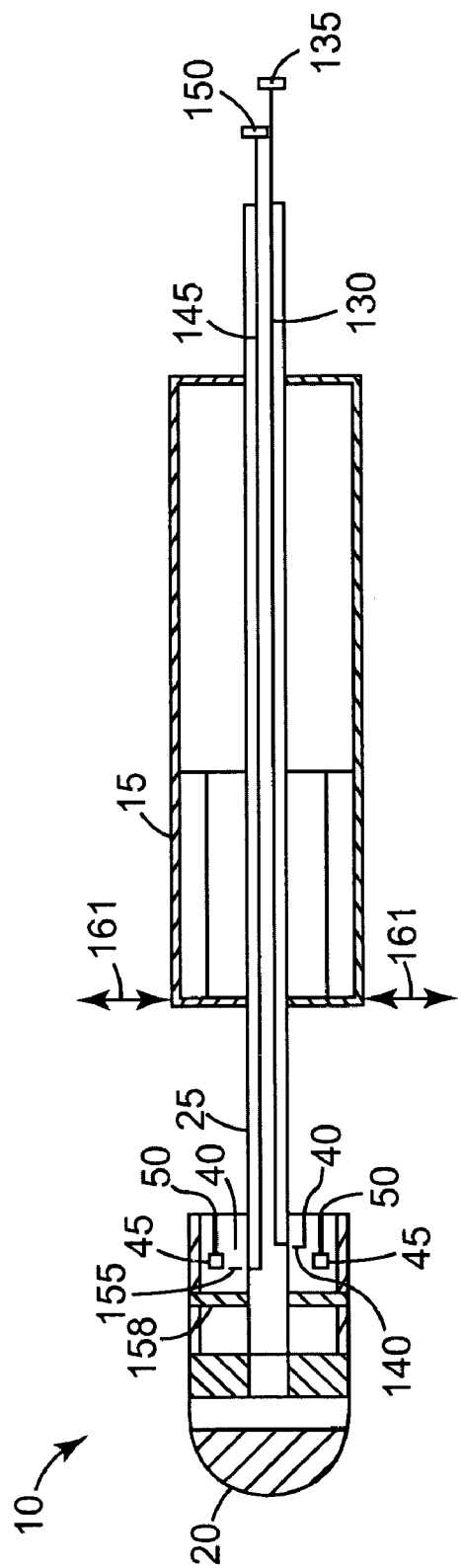
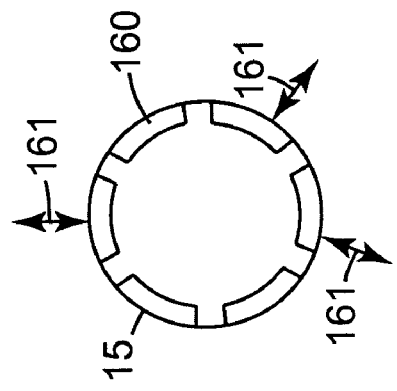
Fig. 4A
Fig. 4B

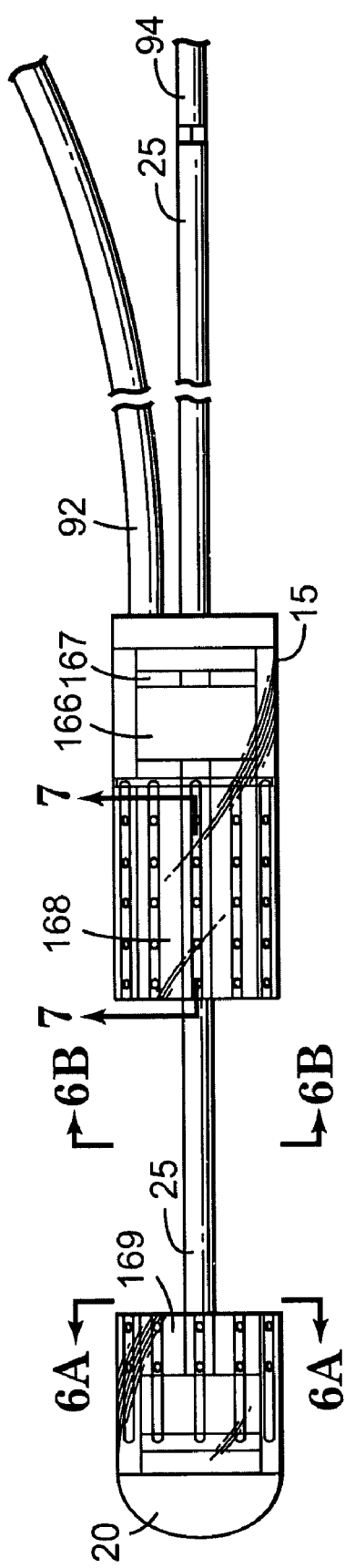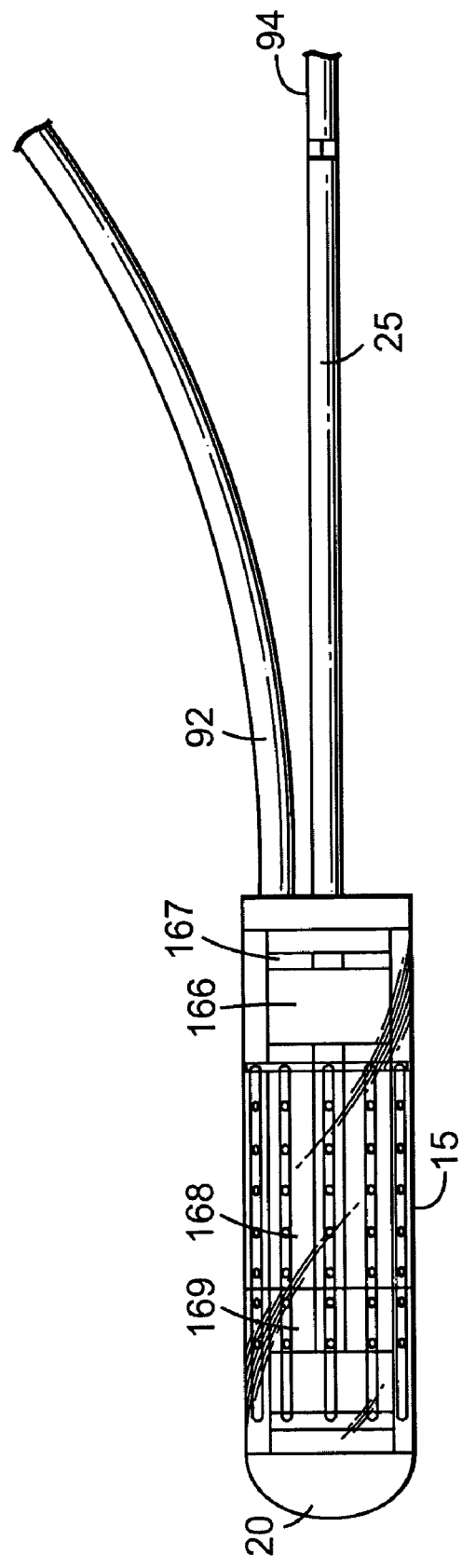

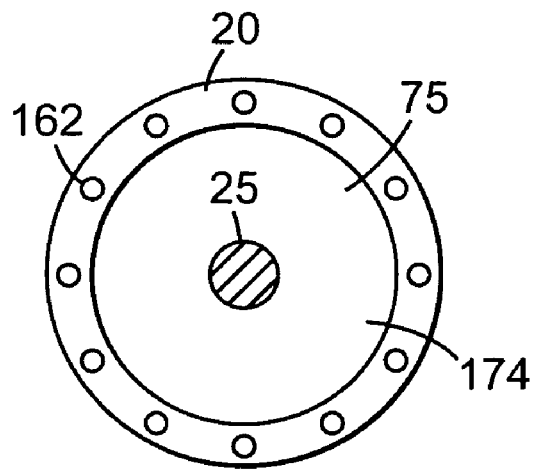 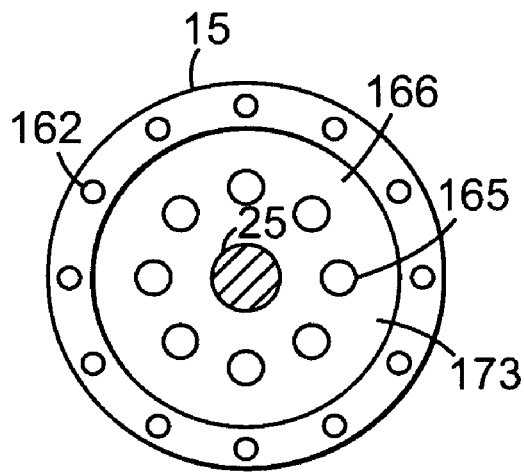
Fig. 6A            Fig. 6B
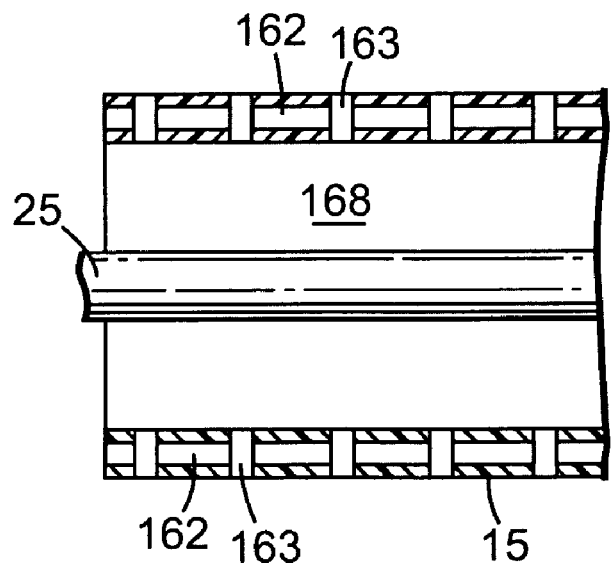
Fig. 7

RESECTION AND ANASTOMOSIS DEVICES AND METHODS

CROSS-REFERENCE TO RELEATED APPLICATIONS

The subject matter of this application is related to the subject matter of U.S. Provisional Patent Application No. 60/375,148, filed Apr. 24, 2002, priority to which is claimed under 35 U.S.C. § 119(e) and which is incorporated herein by reference. The subject matter of this application is also related to the subject matter of U.S. patent application Ser. No. 09/939,052, which is incorporated herein by reference, and of U.S. Pat. Nos. 6,149,667 and 6,517,566, which are incorporated herein by reference.

BACKGROUND OF THE INVENTION

Current therapies for intestinal-tract lesions such as carcinomas, inflammatory lesions, obstructing lesions, and vascular lesions, to name several examples, use a surgical incision for exploration of the abdominal cavity, or a surgical incision large enough to accommodate a surgeon's hand in the case of a laparoscopically assisted resection. Many such procedures involve open/endoscopic surgery and are significantly invasive, requiring general anesthesia and hospitalization. Significant trauma to e.g. the pelvic or abdominal region can result.

Existing known devices to perform an anastomosis on e.g. the colon require a surgeon to dissect the diseased portion of the colon, secure the separable ends of the anastomosis device into the healthy portions of the colon with purse string sutures, bring the device ends together, and perform the anastomosis. Such devices are potentially complex to operate and provide other disadvantages. Additionally, many resection and anastomosis procedures potentially cause contamination of e.g. the abdominal cavity. If an intestinal lesion to be resected is cancerous, for example, spillage of cancer cells into the abdominal cavity is extremely disadvantageous. Introduction of bacteria or lumenal contents outside of the colon or other anatomical structure, into the abdominal cavity or other region or organ, also is undesirable.

SUMMARY OF THE INVENTION

According to embodiments of the invention, an apparatus for moving a diseased portion of an anatomical structure with respect to a healthy portion of an anatomical structure includes a first vacuum section adapted to apply vacuum force to and hold the healthy portion, and a second vacuum section adapted to apply vacuum force to and hold the diseased portion, wherein the second vacuum section is adapted to withdraw within the first vacuum section.

This summary is intended only to describe certain selected features and embodiments of the invention; other features and advantages according to the invention will be apparent from the remainder of this patent application.

BRIEF DESCRIPTION OF THE DRAWINGS

Embodiments of the invention will be described with respect to the figures, in which like reference numerals denote like elements, and in which:

FIG. 1 is a side view of a resection and anastomosis device according to an embodiment of the invention;

FIG. 2 is an end view of a portion of the FIG. 1 device;

FIG. 3 is an end view of a portion of the FIG. 1 device;

FIG. 4A is a cross-sectional view of the FIG. 1 device;

FIG. 4B is an end view of a portion of the FIG. 1 device according to an alternative embodiment;

FIG. 5B is a side view of the FIG. 5A device in an open configuration;

FIG. 5C is a side view of the FIG. 5A device in a closed configuration;

FIG. 6A is an end view taken along line 6A—6A of FIG. 5B;

FIG. 6B is an end view taken along line 6B—6B of FIG. 5B;

FIG. 7 is a cross-sectional view taken along line 7—7 of FIG. 5B;

DETAILED DESCRIPTION OF PREFERRED EMBODIMENTS

Figure 5A:
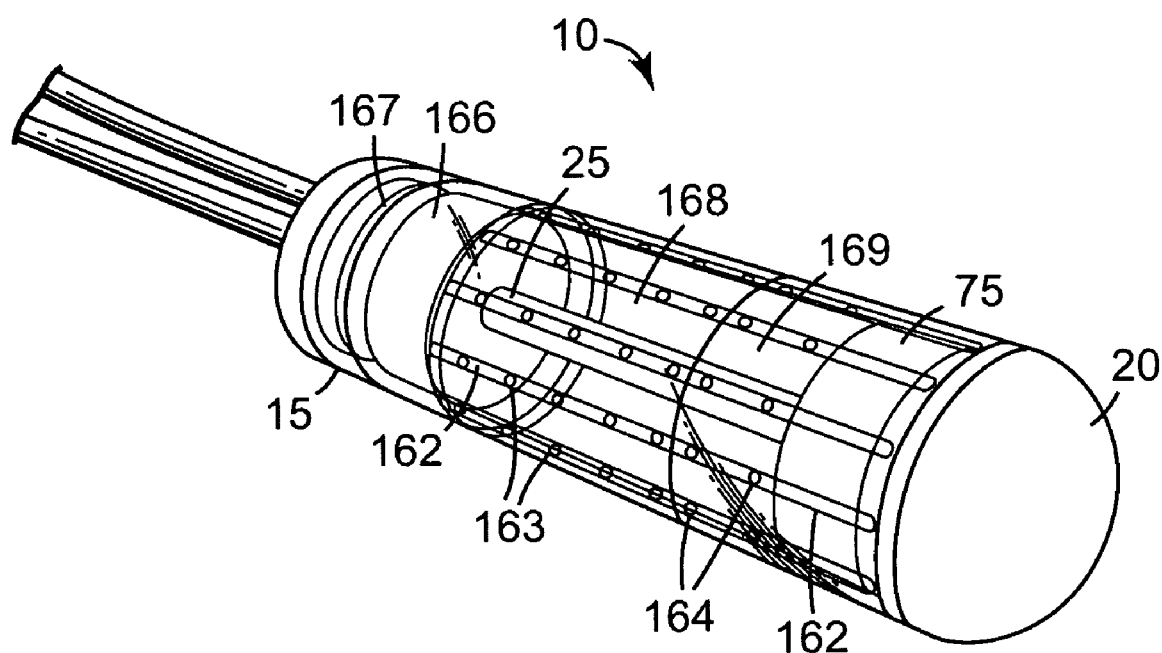
FIG. 5A is a perspective view of a resection and anastomosis device according to an embodiment of the invention.

Embodiments of the invention provide a device for performing an anastomosis and resection of the colon or similar tissue. The anastomosis and resection device includes separable distal and proximal ends connected by a center tube. According to particular embodiments, the center tube also is separable from at least the proximal end. Tubes connect to each end to allow vacuum to be drawn within distal and proximal cavities independently. Annular stapling and resecting capabilities are incorporated within the lumen of the device.

An anastomosis and resection procedure is performed using the device as an endolumenal device and combined with laparoscopic surgical techniques. To perform an anastomosis, the device is placed through the anus into the colon, so that the distal and proximal portions span diseased tissue. The mesentery is dissected from the diseased portion of the colon and removed laparoscopically. Vacuum is applied to the distal and proximal cavities of the device to pull diseased tissue into one or both of the cavities. The diseased tissue is involuted and fills the cavities, allowing the proximal and distal portions to be brought together with the diseased tissue captured within the device. Stapling of the approximated, healthy tissue is then performed. An annular cutter then resects the healthy tissue from the diseased tissue. The vacuum is released, and the device and trapped diseased tissue are removed from the colon.

Anastomosis and resection of the colon using particular embodiments of procedures and devices described herein are accomplished with the anatomical structure being completely closed. In the case where the lesion is cancerous, for example, spillage of cancer cells or lumenal contents outside of the colon is prevented. Further, because the anatomical structure remains closed during the procedure, introduction of bacteria into the abdominal cavity is avoided. It is also unnecessary for a surgeon's hand to be placed into the abdominal cavity, allowing a smaller surgical wound. Additionally, the device offers advantages for use in a patient with a narrow pelvis, e.g. where the anastomosis is to be performed close to the anus.

An anastomosis and resection procedure may also be performed using a device according to an embodiment of the invention as an endolumenal device with separable distal and proximal ends initially separated and unconnected. In a case where a large tumor is present and dissection of the diseased portion of the colon or other structure is accomplished, for example, the proximal separable end is used to hold the rectosigmoid closed while the distal separable end is placed into the healthy portions of the colon with e.g. purse string sutures or the like. The proximal and distal ends then are brought together to perform the anastomosis. This feature also is potentially advantageous for a patient with a large tumor and a narrow pelvis, e.g. where the anastomosis is to be performed close to the anus.

Additional features of device and method embodiments according to the invention include: accurate device placement for removal of the lesion, steering of tissue through independent vacuum control to the distal and proximal portions of the device, and means for preventing migration of healthy tissue into the anastomosis site.

As referenced above, current therapies for intestinal-tract lesions such as carcinomas, inflammatory lesions, obstructing lesions, and vascular lesions, to name several examples, use a surgical incision for exploration of the abdominal cavity, or a surgical incision large enough to accommodate a surgeon's hand in the case of a laparoscopically assisted resection. Embodiments of the invention provide intestinal resection or other resection either entirely endolumenally, endoscopically, or with a combination of endoscopic and laparoscopic techniques. Devices and methods described herein are used in conjunction with e.g. enteroscopy, colonoscopy, and other procedures to identify neoplastic, inflammatory, vascular lesions and other types of lesions, and to accomplish resection of those lesions.

A first embodiment of a resection and/or anastomosis device according to an embodiment of the invention is shown in FIGS. 1–4A. Apparatus 10 includes proximal portion 15, distal portion 20 operably coupled with proximal portion 15, and intermediate portion 25 operably coupled with proximal portion 15 and distal portion 20. Intermediate portion 25 is adapted for movement within proximal portion 15, for example by handle 30, which is illustrated schematically in FIG. 1. Intermediate portion 25 is adapted to apply suction by one or more vacuum or suction apertures 35, to attract anatomical tissue in a manner to be described, according to embodiments of the invention. According to other embodiments, intermediate portion 25 is free of vacuum apertures 35.

Device 10 also includes cutting device 40, which includes or is in the form of an annular cutting blade, for example. Cutting device 40 is adapted to cut anatomical tissue, for example anatomical tissue attracted by vacuum apertures 35 of intermediate portion 25. Although FIG. 1 illustrates distal portion 20 of device 10 as supporting cutting device 40, it should also be appreciated that proximal portion 15 instead can support cutting device 40. Additionally, FIG. 1 illustrates a working edge of cutting device 40 as disposed about halfway between intermediate portion 25 and the outermost edge or circumference of distal portion 20, in a radial dimension. It should be appreciated, however, that cutting device 40 also can be constructed such that the working edge thereof is positioned elsewhere, e.g. much closer to the outermost edge or circumference of distal portion 20. Such positioning allows more space or volume for accommodating tissue between intermediate portion 25 and the edge of distal portion 20.

According to the illustrated embodiment, distal portion 20 also supports stapling device 45, adapted to staple anatomical tissue with one or more staples 50. As with cutting device 40, stapling device 45 and staple(s) 50 are supported either by proximal portion 15 or distal portion 20. In the illustrated embodiment, proximal portion 15 supports one or more staple anvils 55 disposed to act as a backstop for each staple 50 fired by stapling device 45. In the case where proximal portion 15 supports stapling device 45, staple anvils 55 are supported on distal portion 20. In either case, stapling device 45 is disposed between cutting device 40 and the outer edge of distal portion 20 or proximal portion 15.

According to embodiments of the invention, at least one of proximal portion 15 and distal portion 20 is adapted to apply suction to attract anatomical tissue. According to the illustrated embodiment, proximal portion 15 defines vacuum apertures 60, and distal portion 20 defines two sets of vacuum apertures 65, 70 for this purpose. Thus, according to the illustrated embodiments, both proximal portion 15 and distal portion 20 are adapted to apply suction to attract anatomical tissue.

As referenced earlier, intermediate portion 25 supports distal portion 20 for movement therewith. Movement of intermediate portion 25 via handle 30 or other movement device causes like movement of distal portion 20. Distal portion 20 includes internal support 75, which is adapted to receive intermediate portion 25. Internal support 75 is in the form of a wall or "bulkhead" defining central aperture 80 for receiving a distal end of intermediate portion 25, according to an aspect of the invention. Central aperture 80 and the distal end of intermediate portion 25 include complimentary threaded sections for that purpose, for example. Support 75 also defines one or more vacuum apertures 85 for transmitting vacuum or suction force from one side of support 75 to another. According to one embodiment, distal portion 20 is adapted to apply suction on opposite sides of support 75 via vacuum apertures 65, 70 to attract anatomical tissue. The distal end of intermediate portion 25 is open to a distal side of support 75, for example, with vacuum force being transferred from intermediate portion 25 to the proximal side of support 75 via vacuum apertures 85. Thus, vacuum or suction force drawn through intermediate portion 25 is applied to vacuum apertures 35, 65 and 70, according to this embodiment.

FIG. 1 schematically illustrates vacuum source 90 and its connections to the remainder of device 10. Source 90 is fluidly coupled to both proximal portion 15 and to intermediate portion 25 of device 10, e.g. via rigid or flexible tubing or other structure 92, 94. Source 90 is directly connected to both proximal portion 15 and intermediate portion 25 via tubing or structure 92, 94, for example, or is directly connected only to one or the other of portions 15, 20 via tubing or structure 92 or 94, vacuum force then being transferred between portions 15, 20 by apertures 35. In either or both cases, proximal portion 15 is fluidly coupled with intermediate portion 25, e.g. through vacuum apertures 35. Those of ordinary skill in the art will appreciate, upon reading this disclosure, the various ways in which vacuum is drawn individually or collectively in proximal portion 15, distal portion 20 and intermediate portion 25, using various fluid flow paths and structure connected to either a powered device such as a pump, or a manual device such as a syringe.

Distal portion 20 defines a blunt or rounded tip 95, according to embodiments of the invention, to promote easy insertion of device 10 into or through an anatomical structure. One or more O-rings 100 are optionally included in proximal portion 15 for providing a fluid-tight seal relative to intermediate portion 25 and/or relative to the ambient atmosphere.

FIGS. 2–3 are inside end views of distal portion 20 and proximal portion 15, respectively. As shown in e.g. FIG. 2, staples 50 are disposed in two or more generally concentric, alternating rows 105, 110, portions of which are shown, although other staple positioning is also contemplated. According to additional embodiments, distal portion 20 and/or proximal portion 15 can support additional vacuum apertures 115, 120, to attract anatomical tissue to the inside ends of distal portion 20 and proximal portion 15, respectively. Cutting blade 40, supported by distal portion 20, is received within blade groove 125 in proximal portion 15, to promote better cutting. Intermediate portion 25 extends longitudinally along device 10 and generally along the anatomical structure into which device 10 is to be inserted, as will be explained.

Vacuum apertures 60 of proximal portion 15 together define a total cross-sectional area. Proximal portion 15 also defines ring-shaped longitudinal opening 126 (FIG. 3) between the outer circumference of intermediate portion 25 and the inner circumference of proximal portion 15, e.g. at or just to the inside of blade groove 125. Device 10 draws tissue through opening 126 by suction into the interior of proximal portion 15, according to certain embodiments of the invention. To firmly hold tissue on the outer circumference of proximal portion 15, aspects of the invention provide that the total cross-sectional area of vacuum apertures 60 exceeds the cross-sectional area of the longitudinal opening 126. Consequently, the total force per unit area applied to the tissue is sufficient to hold tissue against the outer circumference of proximal portion 15 without allowing that tissue to be pulled into proximal portion 15 as tissue involution occurs, in a manner to be described. A similar relationship exists between the cross-sectional area of apertures 65 and/or 70 of distal portion 20, and longitudinal opening 128 (FIG. 2) through which tissue passes into the interior of distal portion 20.

FIG. 4A is a cross-sectional view showing schematically how cutting device 40 and stapling device 45 are actuated, according to embodiments of the invention. According to the illustrated embodiment, cutting actuator 130 is operably coupled to e.g. handle 135, trigger, or other mechanism to activate cutting device 40 via mechanical or operative actuation link 140. Stapling actuator 145 is operably coupled to e.g. handle 150, trigger, or other mechanism, to actuate stapling device 45 via mechanical or operative actuation link 155. Both cutting actuator 130 and stapling actuator 145 are disposed at least partially within intermediate portion 25, as shown. According to additional aspects of the invention, a single trigger or other device can be used to fire both cutting device 40 and stapling device 45. Non-simultaneous firing of the two devices, as is desirable in many cases, is achieved by a positive stop or other feature requiring separate manual triggering or other actuation.

FIG. 4A also illustrates support 158 in distal portion 20, which is adapted for movement with intermediate portion 25 with respect to proximal portion 15. Support 158 holds or supports one or both of cutting device 40 and stapling device 45, according to embodiments of the invention.

As illustrated in FIGS. 4A–4B, an embodiment of proximal portion 15 is adapted to expand and contract with respect to the anatomical structure within which device 10 is inserted or with respect to which device 10 is being used. For example, proximal portion 15 includes spring-biased or spring-type movable portions 160, each of which are hinged at or toward a proximal side of portion 15, or otherwise adapted to expand or move back-and-forth radially in the direction of e.g. arrows 161. Moving portions 160 radially outwardly, or allowing them to move radially outwardly, allows a lesion larger than the opening radius of portion 15 to enter the inner cavity in portion 15. Portions 160 then snap back to provide e.g. anvil(s) 55 for staple(s) 50, or vice versa, within the circumference through which the lesion passed. The internal volume of portion 15 is temporarily expanded, as a result, over part of the length or the entire length of portion 15, for allowing entrance of additional tissue. Proximal portion 15 is also expanded immediately before distal portion 20 is retracted, according to one aspect, thereby making a larger lumen at the evacuated area and expanding the colon, and providing more space for accommodating tissue or lesion.

FIGS. 5A–8 illustrate an additional embodiment of device 10 according to the invention. The outer shells of distal portion 20 and proximal portion 15, or at least portions thereof, are formed of generally transparent or translucent material, if desired, but alternatively can be opaque. The outer shells of distal portion 20 and proximal portion 15 include vacuum channels 162. Vacuum channels 162 are fluidly connected to vacuum apertures 163, 164 of proximal section 15 and distal section 20, respectively. Vacuum apertures 163, 164 are bi-directional, i.e. they open both to the interior and to the exterior of portions 15, 20. According to alternative embodiments, vacuum apertures 163, 164 are unidirectional and open only to the interior or exterior instead of both. Vacuum apertures 163 of proximal section 15 are fluidly coupled to one or more internal vacuum apertures 165 extending through support 166. Mandrel or intermediate portion 25 slides within support 166 for extension and retraction of distal portion 20. Vacuum apertures 165 through support 166 are in turn fluidly coupled with internal vacuum chamber 167 and then to vacuum source 90, in a manner previously described. Mandrel 25 also is connected to vacuum source 90 (or a different vacuum source, as previously described) for communication of suction force to vacuum apertures 164 of distal portion 20, via vacuum channels 162 and/or via apertures 85 through internal support 75, also as previously described.

Device 10 of FIGS. 5A–8 is free of apertures 35 in intermediate portion 25. Alternatively, intermediate portions 25 can include apertures 35, in the manner of previous embodiments. Device 10 is also free of cutting device 40 or stapling device 45. These devices are optionally provided near the outer walls of proximal portion 15 and/or distal portion 20, in the manner previously described. Alternatively, laparoscopic methods are used to secure the anastomosis created by device 10, and/or a separate blade or other cutting device is used in conjunction with device 10, to maintain device 10 free of cutting device 40 or stapling device 45. FIG. 5B shows the FIG. 5A device in an open configuration. FIG. 5C shows the FIG. 5A device in a closed configuration.

Proximal portion 15 defines internal vacuum chamber 168, and distal portion 20 defines internal vacuum chamber 169. Vacuum apertures 163, being at least partially inwardly directed, draw anatomical tissue into both chambers 168, 169, in a manner to be described, to create a double or two-sided involution. Predetermining or adjusting the relative sizes of chambers 168, 169 varies the degree of suction force applied to drawn-in tissue. Such variation determines the order in which tissue is moved, i.e. whether tissue is moved first into distal portion 20 or proximal portion 15, or whether tissue movement occurs simultaneously. According to the illustrated embodiment, the relatively smaller size of vacuum chamber 169 causes tissue to be drawn first into distal portion 20. Alternatively, or additionally, the degree of suction force applied to e.g. proximal portion 15 and/or distal portion 20 individually from vacuum source(s) 90 is adjusted for the same purpose or a different purpose. The vacuum source(s) thus is/are essentially throttled between the two chambers 168, 169, if desired. For example, if distal vacuum chamber 169 is evacuated more quickly than proximal vacuum chamber 168, e.g. by providing a higher air flow rate to/from chamber 169, tissue generally will be driven in the direction of chamber 169 first. Adjusting chamber size and/or vacuum speed between the chambers effectively controls speed and/or direction of movement of tissue, as well as how much tissue is moved or trapped in proximal portion 15 and distal portion 20. This feature effectively allows compensation for any centering or other errors made in placing device 10 in relation to the lesion. Additionally, if e.g. intermediate portion 25 is sufficiently lubricated, suction force applied through apertures 163, 164 alone is enough to retract distal portion 20 with respect to proximal portion 15 to create the anastomosis, i.e. without separate manual or other retraction force applied to e.g. intermediate portion 25 or handle 30.

Figure 5D:
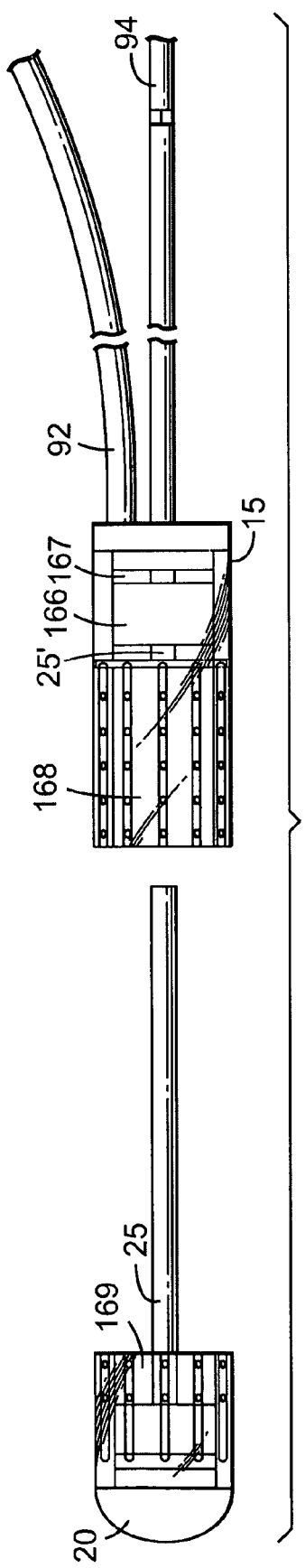
FIG. 5D is a side view of a resection and anastomosis device according to an embodiment of the invention.

FIG. 5D shows an embodiment according to which distal portion 20 and intermediate portion 25 are completely separable and disconnectable from proximal portion 15. Intermediate portion 25 is adapted to snap or otherwise fit into aperture 25' within proximal portion 15, to form an air-tight seal therewith for application of vacuum through intermediate portion 25 to distal portion 20. Aperture 25' is fluidly coupled with rigid or flexible tubing or other structure 94.

Figure 8:
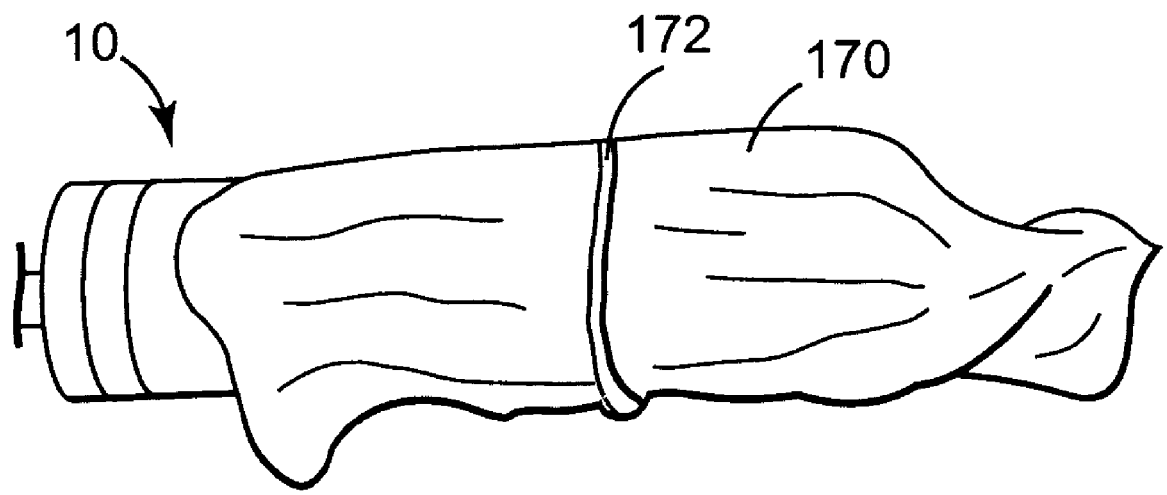
FIG. 8 is a side view of the FIG. 5A device with a portion of anatomical tissue.

FIG. 8 shows device 10 within an experimental portion of anatomical tissue or structure 170, drawn together to create an anastomosis at 172. Additional aspects of the embodiment illustrated in FIGS. 5A–8, including process aspects, will be described with respect to FIGS. 9–18B generally, and FIGS. 18A–18B in particular.

Vacuum apertures 163 of proximal portion 15 together define a total cross-sectional area. The longitudinal opening 173 (FIG. 6B) of proximal portion 15, through which tissue passes, also defines a total cross-sectional area, e.g. the area of a ring-shaped opening defined between the outer circumference of intermediate portion 25 and the interior circumference of proximal portion 15. To firmly hold tissue on the outer circumference of proximal portion 15, aspects of the invention provide that the total cross-sectional area of vacuum apertures 163 exceeds the cross-sectional area of the longitudinal opening 173 of portion 15 through which tissue passes. Consequently, the total force per unit area applied to the tissue is sufficient to hold tissue against the outer circumference of proximal portion 15 without allowing that tissue to be pulled into proximal portion 15 as tissue involution occurs. A similar relationship exists between the cross-sectional area of apertures 164 of distal portion 20, and longitudinal opening 174 (FIG. 6A) through which tissue passes into the interior of distal portion 20.

Device 10 in its various aspects is an apparatus for moving a diseased portion of an anatomical structure with respect to a healthy portion of an anatomical structure. Proximal portion 15 is a first vacuum section adapted to apply vacuum force to and hold the healthy portion. Intermediate portion 25 is a second vacuum section adapted to apply vacuum force to and hold the diseased portion. Second vacuum section 25 is adapted to withdraw within first vacuum section 15. Second vacuum section 25 is adapted to draw the diseased portion into contact with the second vacuum section 25 and to withdraw the diseased portion of the anatomical structure within the healthy portion. The healthy portion is considered a first healthy portion of the anatomical structure, and device 10 further includes third vacuum section 20 operably coupled with first vacuum section 15 and second vacuum section 25. Third vacuum section 20 is adapted to apply vacuum force to and hold a second healthy portion of the anatomical structure disposed on an opposite side of the diseased portion relative to the first healthy portion. Third vacuum section 20 is attached to second vacuum section 25 for movement therewith with respect to first vacuum section 15. Third vacuum section 20 includes cutting device 40, e.g. in the form of an annular cutting blade. Third vacuum section 20 also includes stapling device 45 adapted to fire at least one staple 50 into the anatomical structure.

First vacuum section 15 and second vacuum section 25 are fluidly coupled with common vacuum source 90, as illustrated. Alternatively, they are connected to separate vacuum sources or to a common vacuum source in a manner different than that illustrated in FIG. 1. According to the FIG. 1 embodiment, vacuum source 90 is directly connected to first vacuum section 15 and second vacuum section 25. Alternatively, vacuum source 90 creates vacuum force within first vacuum section 15, and device 10 is adapted to transmit the vacuum force from first vacuum section 15 to second vacuum section 25, e.g. by vacuum apertures 35.

According to embodiments of the invention, first vacuum section 15 is a generally hollow cylindrical member defining a first diameter. Second vacuum section 25 is also a generally hollow cylindrical member, defining a second diameter. The second diameter is less than about 60% of the first diameter, more specifically less than about 40% of the first diameter, and even more specifically, about 20% or less than about 20% of the first diameter, to help ensure that enough space exists for anatomical tissue or lesion to enter the space between first vacuum section 15 and second vacuum section 25, for example between blade groove 125 of first vacuum section 15, if a blade groove is provided, and the outer circumference of second vacuum section 25. Any or all of vacuum sections 15, 20, 25 can be of any desired shape, e.g. elliptical, oval, rectangular, polygonal, triangular or other shape in cross section, to provide a larger tissue- or lesion-accommodating opening in one area or dimension to accommodate the shape of a particular lesion or other tissue to be resected.

Additionally, first vacuum section 15 is considered a first means for holding, and second vacuum section 25 a second means for holding. Both means for holding 15, 25 are for holding anatomical tissue, second means for holding 25 being adapted for movement within first means for holding 15 such that anatomical tissue is moved into first means for holding 15. In an extended configuration, at least a portion of second means for holding 25 extends beyond first means for holding 15. That portion defines a transverse cross-sectional area that is less than about one quarter of a cross-sectional area defined by the first means for holding 15, with respect to e.g. FIG. 3.

First vacuum section 15 and second vacuum section 25 are adapted for placement along a longitudinal direction of the anatomical structure to be treated. Vacuum apertures 35 of second vacuum section 25 are disposed relative to each other along the longitudinal direction, as shown, as well as in a circumferential direction. First vacuum section 15 also defines a plurality of vacuum apertures disposed relative to each other along the longitudinal direction and along a circumferential direction, as does distal portion 20. First vacuum section 15 is adapted to hold the healthy portion of the anatomical tissue against movement while second vacuum section 25 is withdrawn within first vacuum section 15, as will be described.

Methods of use according to any one or more of the apparatus embodiments described herein now will be described with respect to e.g. FIGS. 9–18B. A resection method according to an embodiment of the invention includes inserting resection device 10 into anatomical structure 170 to be resected. Anatomical structure 170 is any structure in which resection and/or anastomosis are needed. Generally tubular anatomical structures are especially advantageous, e.g. colon, small intestine, duodenum, stomach, esophagus, arteries, veins, fallopian tubes, vas deferens, etc. Anatomical structure 170 includes first healthy portion 175, diseased portion 180, in the form of e.g. a lesion, obstruction or other abnormality, and second healthy portion 185, disposed on an opposite side of diseased portion 180 relative to first healthy portion 175.

An appropriate section of anatomical structure 170 is mobilized, e.g. laparoscopically. This portion of the procedure involves division of the line of Toldt, according to one example. Device 10 is inserted into anatomical structure. During insertion, first portion 25 of device 10 is in a retracted position with respect to second portion 15 of device 10, if desired, in the manner of e.g. FIG. 5C. Distal portion 10 thus is near or adjacent to proximal portion 15.

At this point or another point in the procedure, the mesocolon, mesentery or other connective tissue supporting anatomical structure 170, at least in the region of lesion 180, is divided. In the case of the mesocolon or mesentery, a laparoscopic vascular stapler is employed, for example. The mesocolon or mesentery then is removed via e.g. a laparoscopy port site. Mesentery 190 is illustrated in e.g. FIG. 11.

Figure 9:
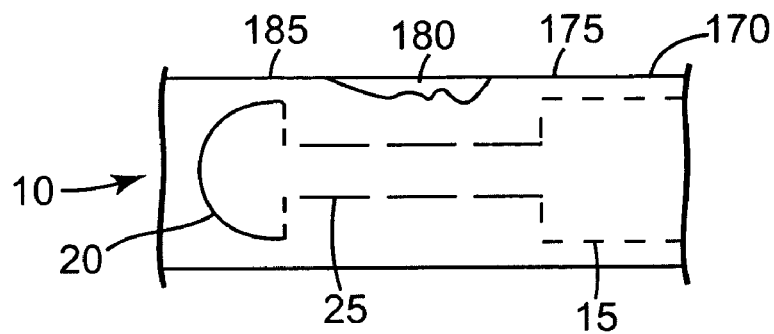
FIGS. 9–17 show apparatus and process steps, according to embodiments of the invention.
Figure 10:
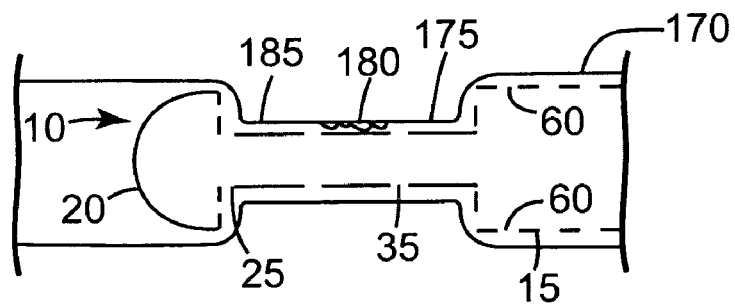
Figure 11:
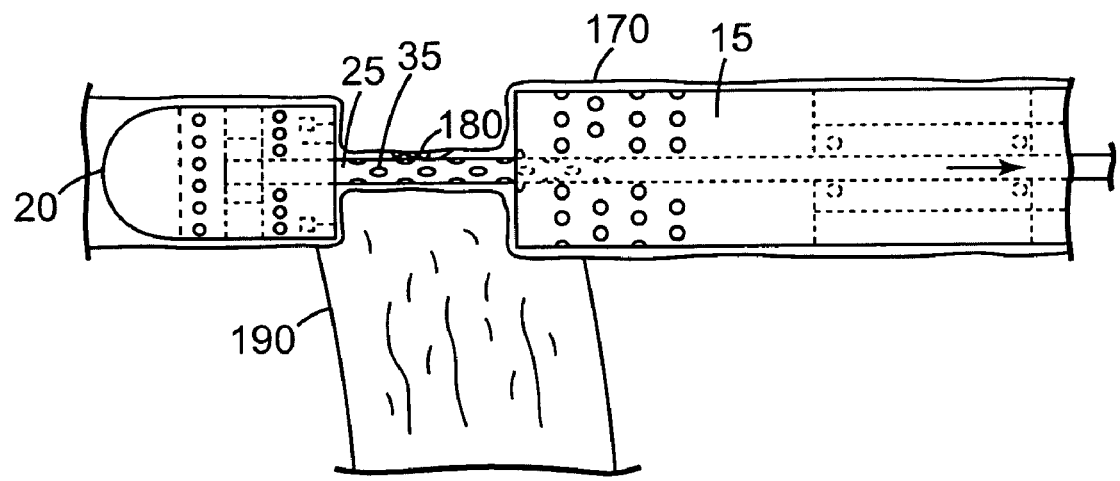

First portion 25 is extended relative to second portion 15, as shown in e.g. FIGS. 9–10. Device 10 is placed such that first portion 25 of device 10 is adjacent to lesion 180, with third portion 20 and second portion 15 on either side of lesion 180 such that an appropriate margin of healthy tissue 170, 185 is on either side of lesion 180. Methods of illuminating and marking anatomical structure 170 for accurate placement of device 10 are contemplated and will be described with respect to FIGS. 19–21, below.

According to embodiments of the invention in which anatomical tissue, e.g. lesion 180, is to be drawn into both distal portion 20 and proximal portion 15 of device 10, device 10 is positioned such that lesion 180 is either centered between proximal portion 15 and distal portion 20, or such that lesion 180 is either in a far-proximal or far-distal configuration with respect to proximal portion 15 and distal portion 20, e.g. such that lesion 180 is adjacent or beyond proximal portion 15 or distal portion 20. Note e.g. FIGS. 39–43, described below.

Once placed, device 10 is ready to move anatomical structure 170 into a desired position for resection and anastomosis. According to embodiments of the invention, structure 170 is initially moved toward or into any one or more of proximal portion 15, distal portion 20, and intermediate portion 25. To move structure 170 toward intermediate portion 25, for example, suction or vacuum force is applied through vacuum apertures 35. To move structure 170 into or toward proximal portion 15, suction or vacuum force is applied through vacuum apertures 60 or 163. To move structure 170 into or toward distal portion 20, suction or vacuum force is applied through vacuum apertures 65, 70 or 164. Ultimately, lesion 180 and at least a portion of healthy tissue 175, 185 surrounding lesion 180 are drawn toward intermediate portion 25, for example into contact with intermediate portion 25, into contact with an external surface of distal portion 20 and/or proximal portion 15, and/or into an interior portion of distal portion 20 and/or proximal portion 15. According to the illustrated embodiment, proximal portion 15 of device 10 is used to hold a portion of anatomical structure 170 against movement while first portion 25 is retracted, according to one example. Suction is used to move anatomical structure 170 toward both intermediate portion 25 and proximal portion 15 of device 10.

Figure 12:
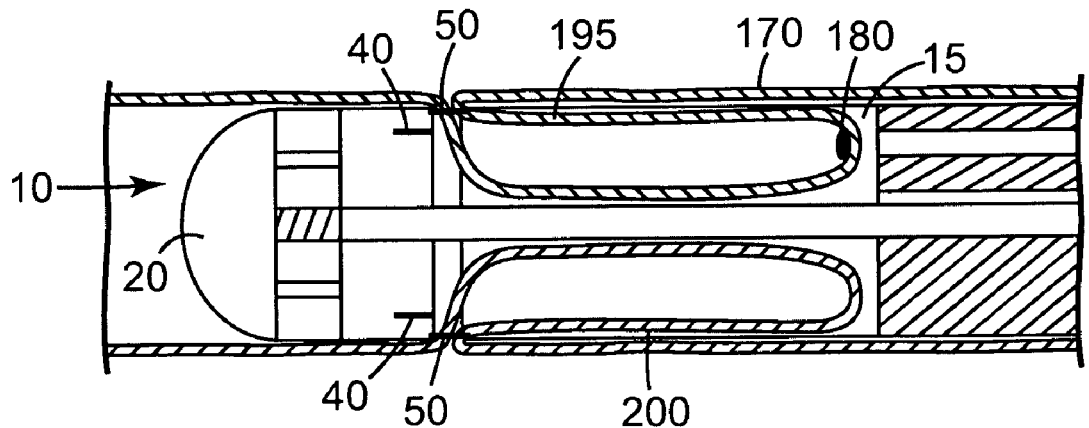
Figure 13:
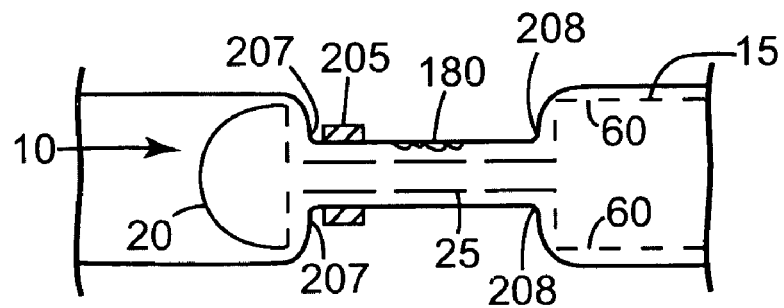
Figure 14:
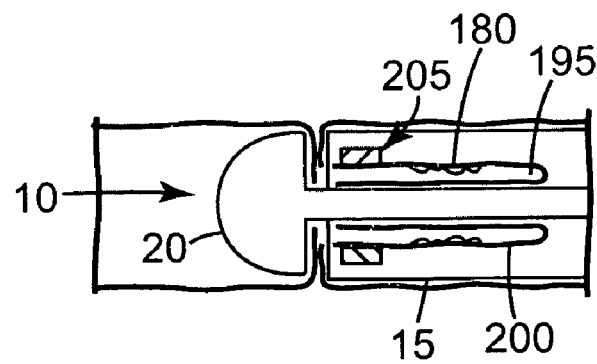

With device 10 holding anatomical structure 170 in a desired configuration, involution of structure 170 within device 10 occurs. According to one embodiment, shown in e.g. FIG. 12, structure 170 is involuted by retracting intermediate portion 25 into proximal portion 15. The involuting step creates at least one involuted section of anatomical structure 170. Upper and lower portions 195, 200 of an involuted section are represented in FIG. 12, for example, drawn within proximal portion 15 of device 10. According to other embodiments, an involuted section is created in distal portion 20, alone or in combination with the involuted section in proximal portion 15. Additionally, if appropriate external and/or internal surfaces of device 10 are properly lubricated, involution occurs automatically upon application of vacuum. In other words, application of vacuum itself draws structure 170 into distal portion 20 and/or proximal portion 15, and/or causes intermediate portion 25 to retract into proximal portion 15, if desired.

At an appropriate point in the procedure, structure 170 is permanently shortened, generally by the length of the involuted section, e.g. by using stapling device 45 to fire one or more staples 50. An anastomosis between the healthy portions of anatomical structure 170 thus is created. Involuted section 195, 200 with lesion 180 or other diseased portion then is cut away, by firing cutting device 40. The stapling and cutting functions also can occur simultaneously, for example by actuating a single trigger or other actuation mechanism. Involuted section 195, 200 then is withdrawn with device 10 as device 10 is withdrawn from anatomical structure 170. Lesion 180 or other diseased portion is withdrawn without exposure to the abdominal cavity or other environment surrounding anatomical structure 170.

Resection and anastomosis procedures according to embodiments of the invention thus are accomplished with anatomical structure 170 being completely closed. In the case where lesion 180 is a cancerous lesion, spillage of cancer cells or lumenal contents outside anatomical structure 170 is prevented. Further, because anatomical structure 170 remains generally closed, introduction of bacteria into e.g. the abdominal cavity also is generally prevented. Still further, embodiments of the invention do not require a surgeon's hands to be placed in the abdominal cavity and are usable within a narrow space, e.g. within a narrow pelvis, e.g. that of a male patient. Embodiments of the invention thus provide significant advantages.

Figure 15:
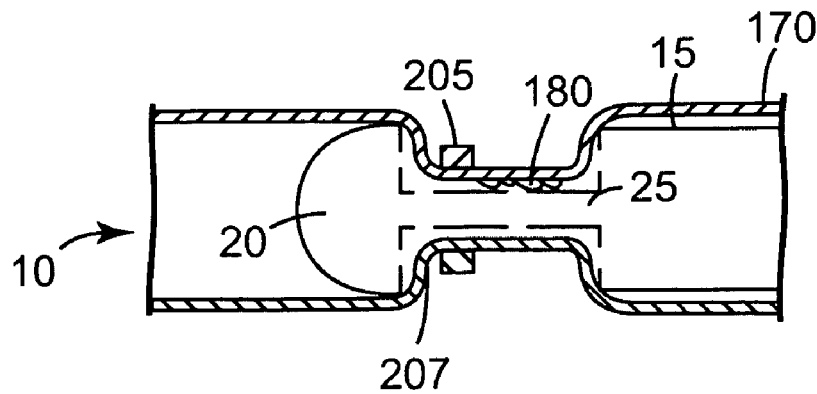
Figure 16:
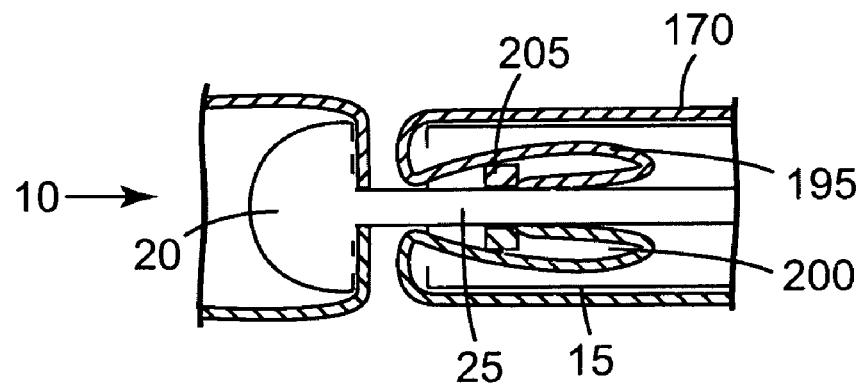
Figure 17:
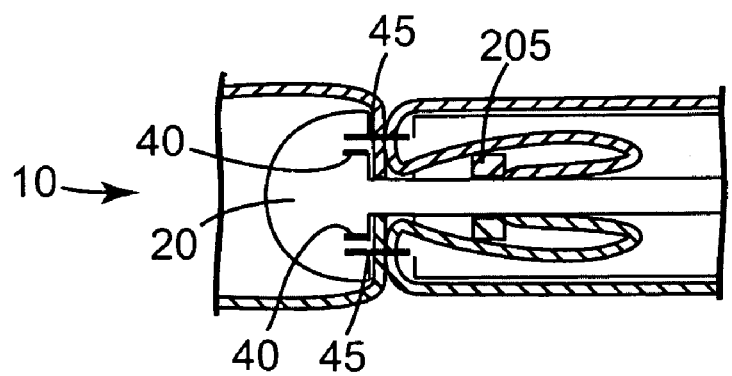

Additional embodiments illustrated in FIGS. 13–17 use a laparoscopic collar, and/or laparoscopically divide the diseased portion of anatomical structure 170. Collar 205 is laparoscopically placed around e.g. the serosal surface of lesion 180 at an appropriate point in the procedure. More than one collar 205, placed e.g. on opposite sides of lesion 180, also can be used if desired. Lesion 180 is divided circumferentially, for example using a laparoscopic cutting device, at either location 207 (FIGS. 13–14), which is near the junction of distal portion 20 and intermediate portion 25, at location 208, which is near the junction of intermediate portion 25 and proximal portion 15, or at both locations 207, 208. Alternatively, anatomical structure 170 is divided at collar 205 (FIGS. 15–17). Wherever structure 170 is divided, vacuum or suction force, and/or collar(s) 205, maintain structure 170 in contact with device 10. Intermediate portion 25 of device 10 is withdrawn into proximal portion 15, and distal portion 20 comes into proximity with proximal portion 15, such that lesion 180, involuted sections 195, 200, and collar(s) 205 all are contained within proximal portion 15. Stapling device 45 is fired to create an anastomosis. Cutting device 40 is eliminated, according to this embodiment, because lesion 180 is divided laparoscopically. Alternatively, cutting device 40 is included and used as with previous embodiments. In both cases, involuted sections 195, 200 are cut away and removed with device 10.

Figure 18A:
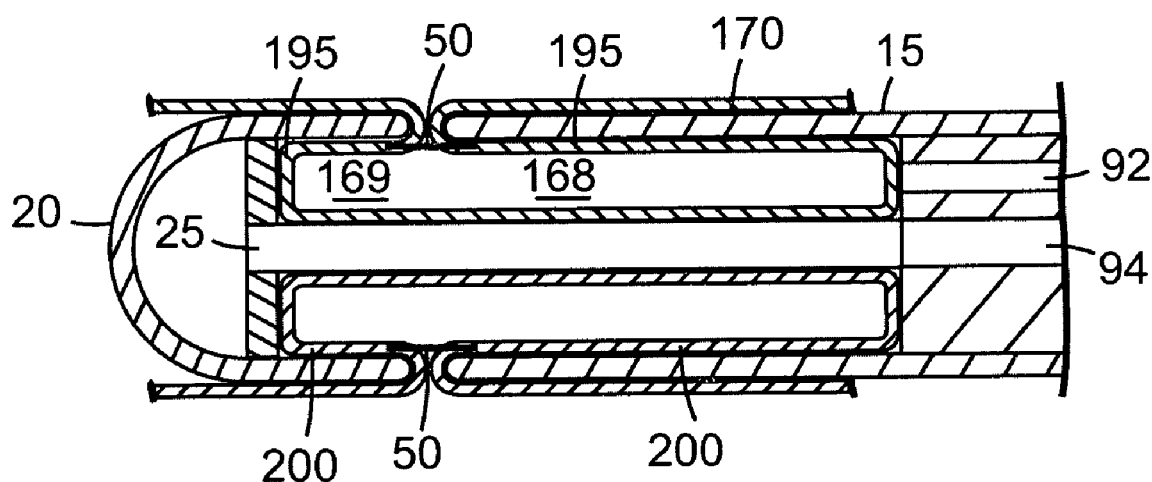
FIG. 18A shows double involution according to embodiments of the invention.

FIG. 18A shows an embodiment akin to that shown in FIGS. 5A–8. Device 10 contains involuted anatomical structure in both distal portion 20 and proximal portion 15, according to this embodiment, although in other embodiments vacuum is applied or the anatomical structure otherwise manipulated such that involuted anatomical structure is present in either distal portion 20 or proximal portion 15. As viewed in the figure, an upper involuted section 195 and a lower involuted section 200 are created, although it should be appreciated that in a three-dimensional sense device 10 creates a single, generally annular or ring-shaped involuted section between portions 15, 20. Cutting device 40 and stapling device 45, if provided, are located very close to the outer wall of e.g. distal portion 20, for example, to increase the radial dimension through which anatomical structure 170 is drawn into distal portion 20. Double involution allows a greater length of anatomical structure 170 to be resected and provides other advantages. Increasing the length of distal portion 20 and/or proximal portion 15 increases the amount of structure 170 that can be involuted and resected.

Figure 18B:
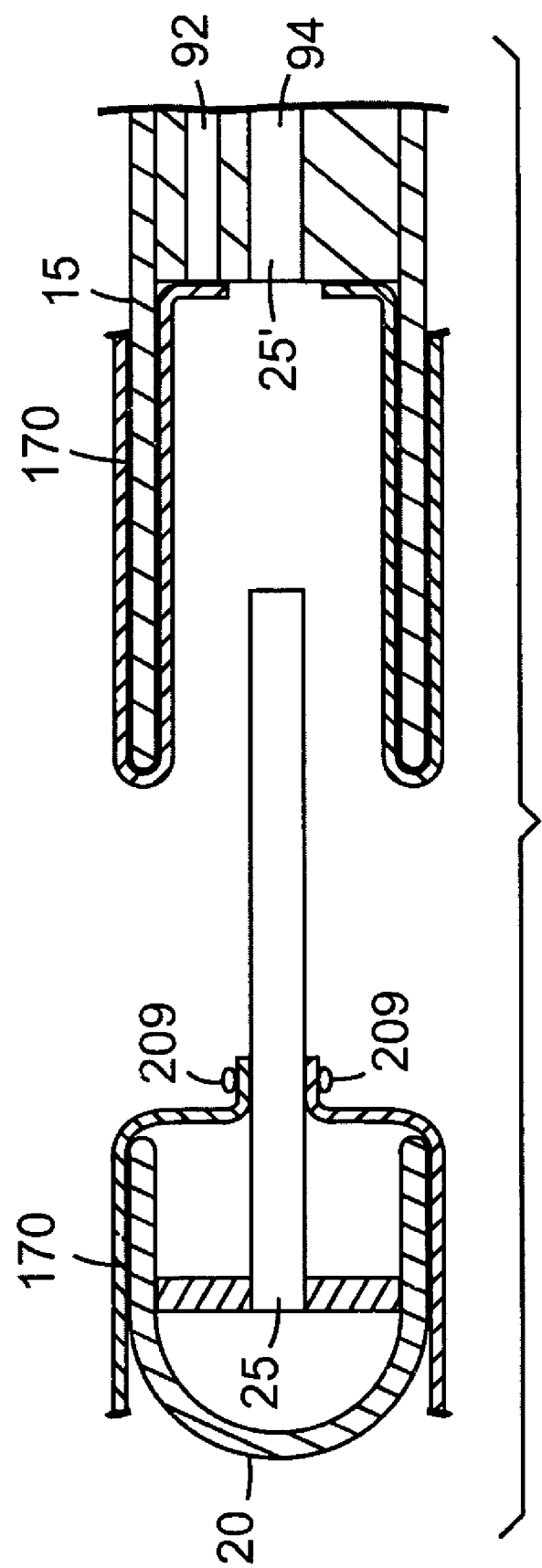
FIG. 18B shows a resection and anastomosis device with separable portions and associated tissue, according to an embodiment of the invention.

FIG. 18B shows an embodiment akin to that shown in FIG. 5D. According to one method of use, the colon or other anatomical structure 170 is clamped and vacuum is applied through tube or other structure 92 in proximal portion 15. Structure 170 collapses and involutes into proximal portion 15, as illustrated. Anatomical structure 170 then is divided by the surgeon, and the lesion or other diseased portion then is removed. Distal portion 20 then is inserted into the open end of anatomical structure 170 and secured with a purse-string 209 suture or the like, such that the end portion of anatomical structure 170 is drawn toward intermediate portion 25, as illustrated in FIG. 18B. Distal portion 20 with attached intermediate portion 25 then is connected to aperture 25'. According to one example, a trocar is directed down the center of tube or other structure 94 and aperture 25'. Intermediate portion 25 is placed over the trocar and guided over the trocar to join and seal with aperture 25'. The trocar then is removed. Vacuum is applied to distal portion 20, involuting anatomical structure 170 into distal portion 20. Distal portion 20 and proximal portion 15 are brought together, e.g. automatically by the applied vacuum, or manually, such that the configuration of FIG. 18A results. As with the embodiment of FIG. 18A, cutting device 40 and stapling device 45, or similar devices, if provided, are used to cut and staple the free ends of anatomical structure 170 within portions 15 and/or 20.

Thus, according to an embodiment of the invention, proximal portion 15 and distal portion 20 are adapted to be disconnected, and proximal portion 15 comprises structure, e.g. aperture 25', for receiving distal portion 20, e.g. tube 25 thereof, such that connection of distal portion 20 to proximal portion 15 via tube 25 initiates or allows involution of anatomical tissue 170 into distal portion 20. According to one embodiment, intermediate portion 25 includes a pointed free end, for penetration of any portion of anatomical structure 170 located in front of aperture 25'. According to additional embodiments, proximal portion 15 is used by itself, without distal portion 20, for use in combination with other procedures, such as linear stapling with a separate linear stapling device, clamping, resection, or other procedures with other devices, to hold e.g. the rectosigmoid, other colon portion, or other anatomical structure 170. Such structure 170 is held in an involuted and/or stable configuration, such that a diseased portion is more easily removed or other procedure is more easily performed.

Additionally, a method according to an embodiment of the invention thus includes inserting first holding device 15 into anatomical structure 170 to be resected, involuting anatomical structure 170 within first holding device 15 by applying vacuum to anatomical structure 170 through first holding device 15, connecting a disconnected second holding device 20, 25 to first holding device 15, applying vacuum to second holding device 20, 25 via first holding device 15, involuting anatomical structure 170 within second holding device 20, 25, and moving first holding device 15 and second holding device 20, 25 toward each other to join anatomical structure 170 held by first holding device 15 with anatomical structure 170 held by second holding device 20, 25. The method also optionally includes tying anatomical structure 170 to second holding device 20, 25, for example by purse-string suture, other suture, or other device, before the moving of first holding device 15 and second holding device 20, 25 toward each other.

Figure 19:
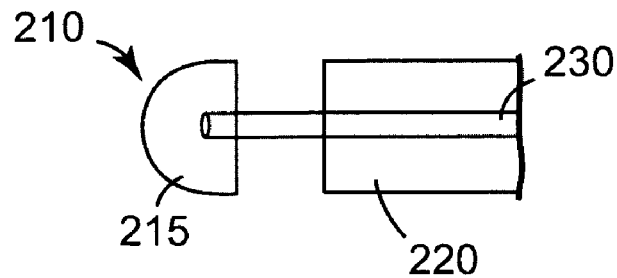
FIG. 19 is a side view of a resection and anastomosis device according to an embodiment of the invention.
Figure 20:
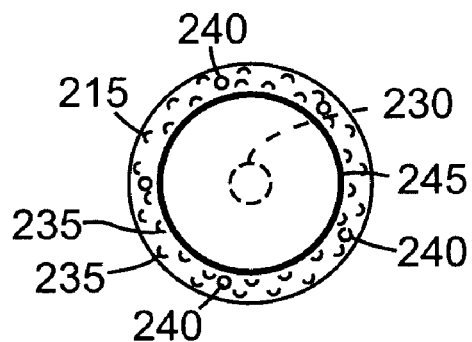
FIG. 20 is an end view of a portion of the FIG. 19 device.

Simplified embodiments of the invention now will be described with respect to e.g. FIGS. 19–21. Features previously described with respect to e.g. any of FIGS. 1–18B generally are equally applicable for use with respect to FIGS. 19–21, and vice versa. Device 210 according to such embodiments includes distal portion 215 and proximal portion 220, supported by mandrel 230. FIG. 20 illustrates the inner face of distal portion 215, which is generally cylindrical according to one embodiment and serves as a staple anvil. Distal cylinder 215 defines staple anvil grooves 235 arranged in e.g. two concentric rows, one or more vacuum ports 240, for example five vacuum ports, and cutting groove 245, which is disposed for receiving a cutting blade from the proximal cylinder to cut tissue. Central mandrel 230 or equivalent vacuum tube, shown in dashed lines, provides vacuum force through ports 240.

Figure 21:
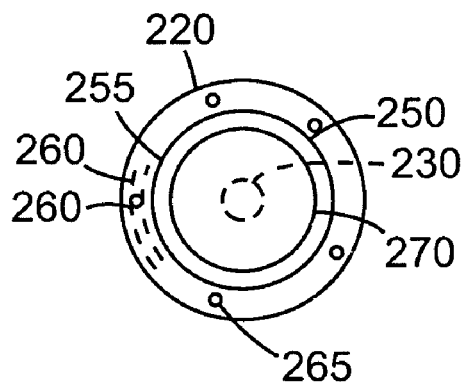
FIG. 21 is an end view of a portion of the FIG. 19 device.
Figure 22:
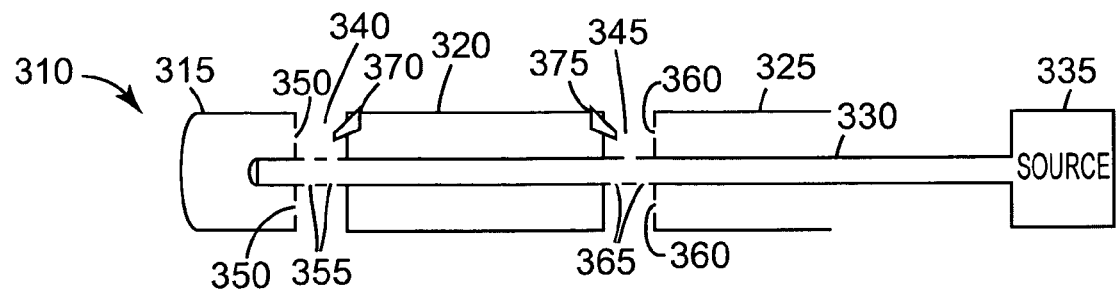
FIGS. 22–25 are schematic side views of a resection and anastomosis device according to an embodiment of the invention.

FIG. 21 illustrates the inner face of proximal portion or cylinder 220. Mandrel 230 or vacuum tube extends centrally. Circular cutting blade 250 is generally fixed with respect to portion 220. Staple and vacuum section 255 contains a staple cartridge, for example one staple cartridge containing multiple staples, for sequentially or simultaneously projecting staples through staple slits 260, which are aligned with staple anvil grooves 235. Staple and vacuum section 255 also includes one or more vacuum ports 265, for example five vacuum ports. Proximal section 220 also contains sleeve or catch tube 270, which according to embodiments of the invention is disposed to slide with respect to proximal section 220.

According to a colonic anastomosis method of use for these and the other embodiments described herein, a lesion or other diseased portion is identified by locating it endoscopically with associated lighting or other illumination. The lesion may be dilated pneumatically, for example, to enlarge the diameter of the colon in that location to better allow passage of device 210. A laparoscopic camera is used to observe light originating within the colon or other anatomical structure, e.g. from a colonoscope light source transmurally or from a fiber optic or other light source associated with device 210. A marker is placed laparoscopically. Device 210 is inserted. Device 210 has e.g. a fiber optic light or other light source for illumination, shining light radially outward. This light is transmitted through the wall of the anatomical structure and is visualized using e.g. a laparoscopic camera. This light is lined up with the previously placed marker. Alternatively, a light source separate from device 210 and laparoscopic camera vision are used. Upon entering the body, cylinders or portions 215, 220 are positioned together and distally on mandrel 230 or other central shaft of device 210. The area of intersection of portions 215, 220 is positioned distal to the lesion, is centered with respect to the lesion, or is positioned proximal to the lesion. In the case where the area of intersection is positioned distal to the lesion, dependent on where the lesion is in the colon, the distance distal to the lesion is as small as about 2 cm or less or as great as about 10 cm or greater. In one case, device 210 is placed with the aid of the previously placed marker, such that the lesion is generally centered between portions 215, 220. Sleeve 270 is retracted such that it is not located between portions 215, 220.

The mesentery is divided with a stapler, harmonic scalpel or other device. Vacuum is applied, in a manner akin to that described in previous embodiments, causing tissue to form to portions 215, 220. Sleeve 270 then is pushed to slide over the diseased section, and portions 215, 220 are drawn together. The proximal tissue is cut with blade 250, an equivalent cautery device or other device. Blade 250 is generally circular and fixed, and manually or otherwise bringing portions 215, 220 together or toward each other accomplishes the cutting, according to embodiments of the invention. Stapling and cutting of the tissue occur, vacuum is released, and device 210 is withdrawn with the diseased tissue trapped within it.

Additional embodiments of the invention now will be described with respect to FIGS. 22–32. Features previously described with respect to e.g. any of FIGS. 1–21 generally are equally applicable for use with respect to FIGS. 22–32, and vice versa. Resection and anastomosis device 310 includes head 315, middle portion 320, and handle or base 325, all connected and supported by mandrel 330. Handle or base 325 is a proximal portion of device 310, according to embodiments of the invention, and head 315 is a distal portion. Mandrel 330 is operatively coupled with vacuum source 335, which is illustrated schematically in FIG. 22 and is either a powered vacuum source, e.g. a pump, or a manual vacuum source, e.g. a syringe or other structure. Mandrel 330 is hollow or otherwise contains one or more passages for applying suction drawn by source 335 to one or more of distal portion 315, middle portion 320, and proximal portion 325. More particularly, mandrel 330 applies suction to one or more voids or indents 340, 345 defined between distal portion 315 and middle portion 320, and middle portion 320 and proximal portion 325, respectively.

According to the illustrated embodiment, distal portion 315 contains or defines one or more vacuum ports 350, and mandrel 330 contains or defines one or more vacuum ports 355, all for applying suction pressure to indent 340. Proximal portion 325 contains or defines one or more vacuum ports 360, and mandrel 330 contains or defines one or more vacuum ports 365, all for applying suction pressure to indent 345. According to alternative embodiments, only mandrel 330 contains vacuum ports instead of additionally including ports in portions 315, 325, or only portions 315, 325 contain vacuum ports instead of additionally including ports in mandrel 330. Additionally, just mandrel 330 includes one or more ports for evacuating one of the two indents 340, 345 and/or just one of the portions 315, 325 includes one or more ports for evacuating the other of the two indents 340, 345. Any arrangement that provides partial or total evacuation of indents 340, 345 is applicable according to embodiments of the invention, such that vacuum is achieved in both the proximal and distal parts of the intestine or other organ or region in which device 310 is used.

Figure 23:
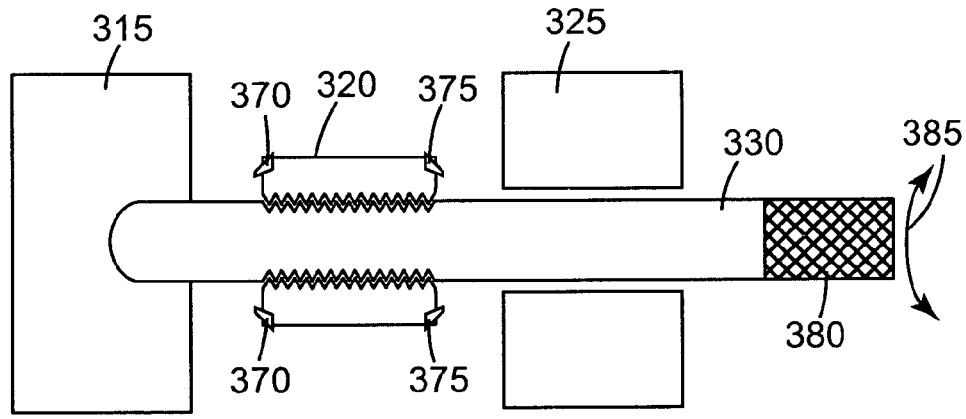
Figure 24:
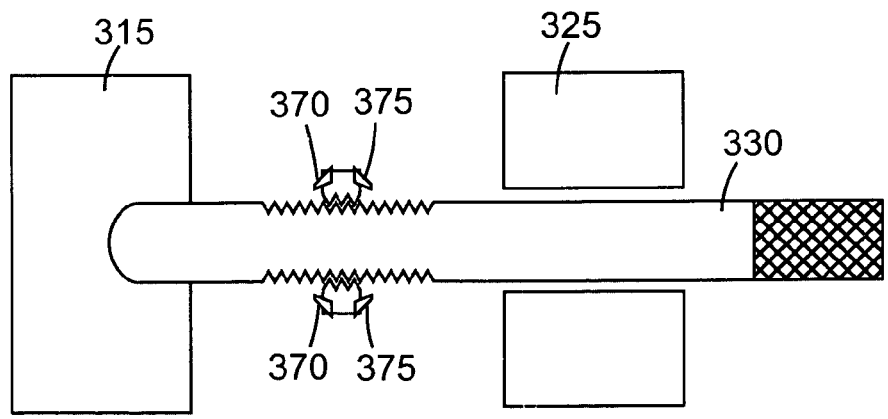
Figure 25:
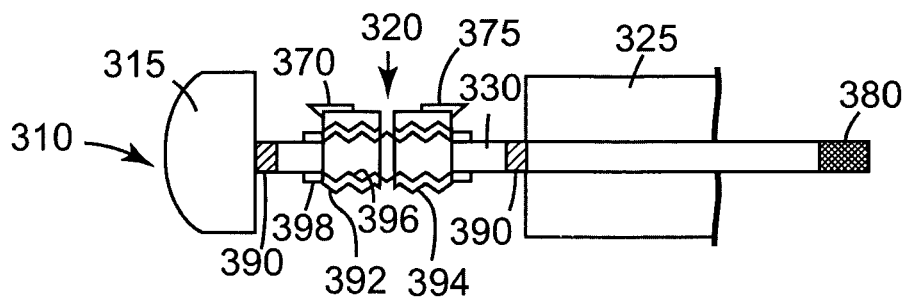

Middle portion 320 supports blades or scalpels 370, 375. Device 310 alternatively incorporates one or more electrocautery devices instead of blades 370, 375. According to embodiments of the invention, blades 370, 375 are retractable and are directed longitudinally, i.e. to the left and to the right as viewed in FIG. 22, along middle portion 320. As shown in the embodiment of FIGS. 23–24, device 310 includes more than one of each blade 370, 375, disposed on opposite sides of middle portion 320. Alternatively, blades 370, 375 are each circular blades, e.g. in the manner described with respect to e.g. FIGS. 19–21.

Mandrel 330 is supported for rotation about its longitudinal axis by rotation of handle 380, as represented by arrow 385. Mandrel 330 is supported with respect to proximal portion 325 and distal portion 315 by respective bearings 390 (FIG. 25), allowing portions 315, 325 to remain stationary while mandrel 330 turns. Mandrel 330 defines or supports two threaded portions 392, 394 for blades 370, 375, respectively. Portions 392, 394 engage threaded portion 396 of mandrel 330. Keyed portion 398 of mandrel 330 causes blades 370, 375 to rotate. Blades 370, 375 are thus actuated to rotate and/or to move between an expanded or deployed configuration (FIG. 23) and a retracted or undeployed configuration (FIG. 24). Structure in the manner of a turnbuckle for adjusting the frame of a fence gate, for example, also is contemplated for use according to embodiments of the invention.

According to other embodiments, middle portion 320 of device 310 is constructed in the manner of a scissors jack.

When threaded portion 396 of mandrel 330 turns, the ends of middle portion 320 are arranged such that middle portion 320 increases or decreases in diameter. Blades 370, 375, attached to the expanding part of middle section 320, then are advanced into a deployed position automatically. Reversing the direction of rotation causes middle portion 320 to contract or collapse and return blades 370, 375 to a non-cutting or undeployed position.

Figure 26:
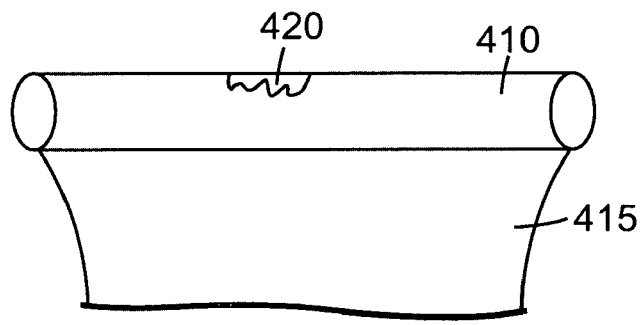
FIG. 26 is an anatomical drawing.

FIG. 26 illustrates segment 410 of intestine or other organ, corresponding mesentery 415, e.g. mesocolon or other supporting/connective structure, and lesion 420.

Figure 27:
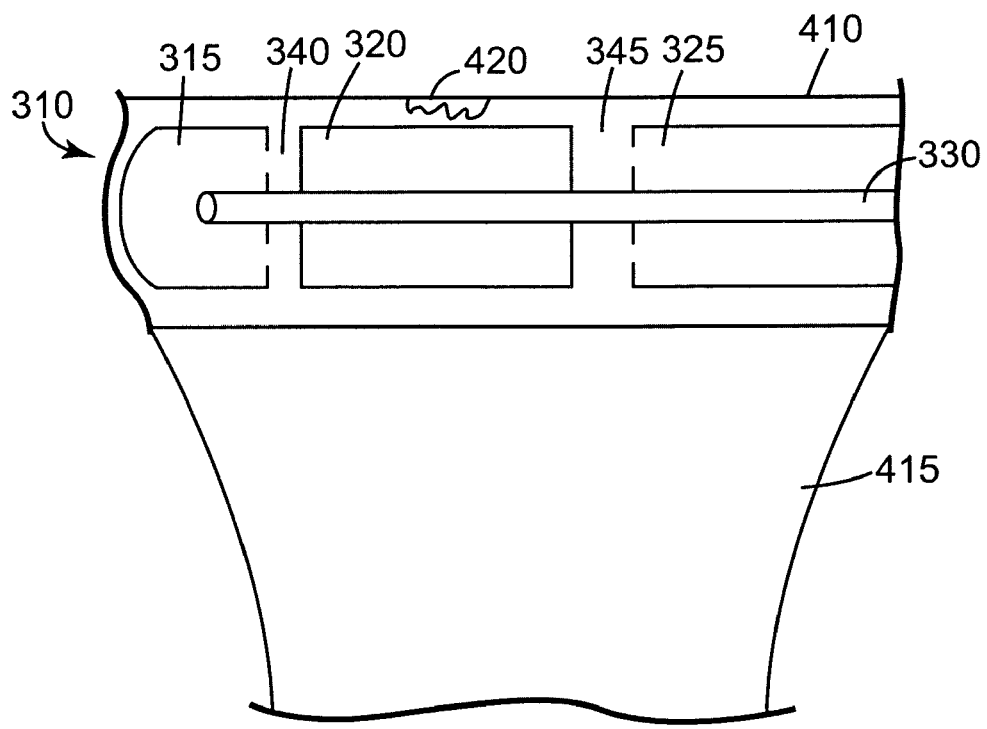
FIGS. 27–32 are side schematic views showing apparatus and method embodiments according to the invention.

In use, with reference first to FIG. 27, device 310 is placed into e.g. the intestinal tract such that lesion 420 is between indents 340, 345, i.e. such that middle portion 320 of device 310 is adjacent lesion 420, or in a distal or proximal configuration as previously described. When lesion 420 is in a position that can be reached by an endoscope, for example any position in the colon, device 310 is placed transanally, according to aspects of the invention. The surgeon or other user of device 310 determines proper placement of device 310 with respect to lesion 420 by e.g. laparoscopic viewing of endolumenal light, as described above, according to one embodiment.

Figure 28:
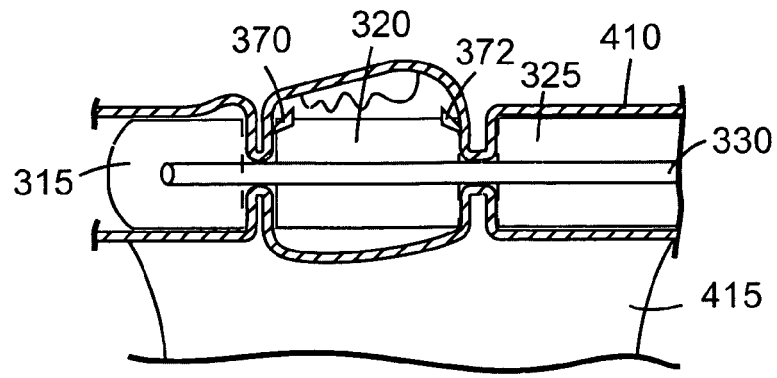
Figure 29:
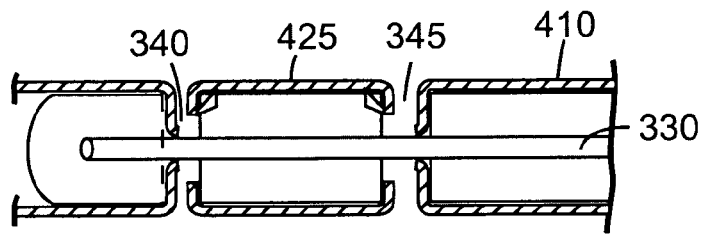

Once device 310 is positioned properly, vacuum source 335 is activated to draw the wall of segment 410 into indents 340, 345, as illustrated in FIG. 28. Blades 370, 375, supported by middle portion 320, are then deployed, in the manner described previously. Once deployed, blades 370, 375 are then rotated to cut the walls of segment 410, as described previously, forming resected portion 425.

Figure 30:
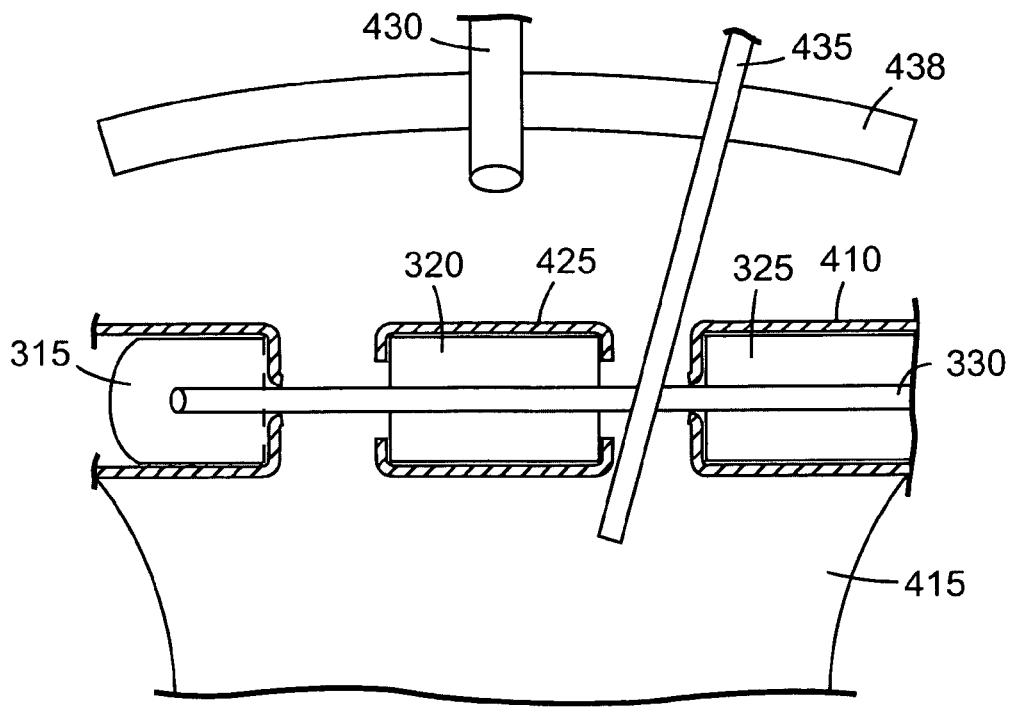
Figure 31:
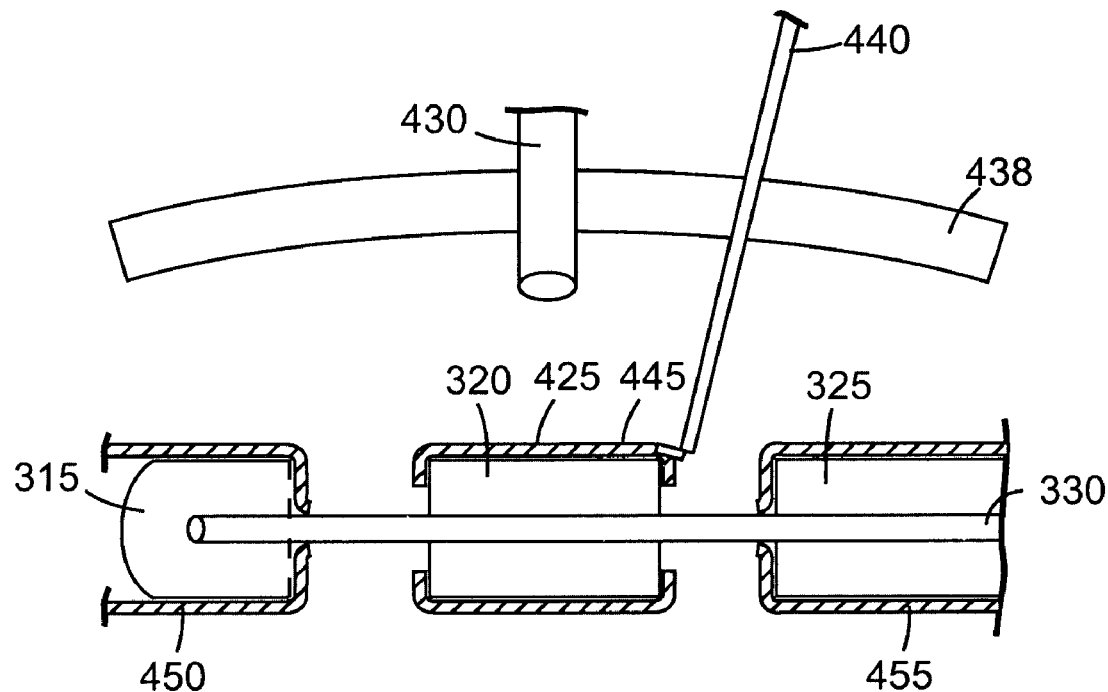

With reference to FIG. 30, laparoscopic camera 430 and blood-vessel ligating device 435, for example a harmonic scalpel or stapling device, are inserted through corresponding ports in e.g. abdominal wall 438 of the patient. Device 435 then is used to divide resected portion 425 of initial segment 410 from its corresponding mesentery, mesocolon or other structure 415. As shown in FIG. 31, electrocautery device 440 then is used to divide antimesenteric border 445 of resected portion 425. Resected portion 425 then is removed via one or more of the port incisions through abdominal wall 438 or other anatomical structure using a suitable instrument.

At this point, middle portion 320 is reduced in diameter such that it can fit within distal portion 315 and/or proximal portion 325. Middle portion 320 is reduced using a screw mechanism that simultaneously elongates middle portion 320 and draws its outer circumference closer to mandrel 330. Once reduced and/or elongated, middle portion 320 is retracted with mandrel 330 into proximal portion or handle 325.

Figure 32:
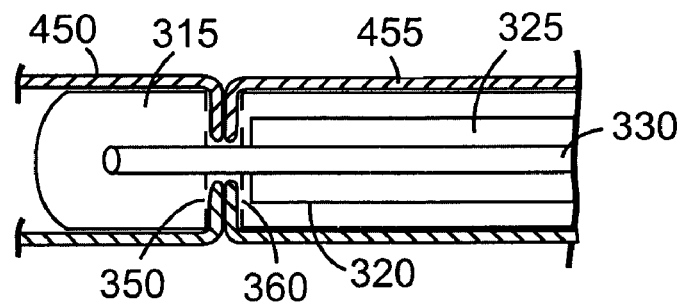

Distal and proximal portions 450, 455 of the remaining intestinal or other anatomical segment 410 become approximated, as shown in FIG. 32. Vacuum source 335 applies vacuum pressure via e.g. vacuum ports 350, 360 to hold segment portions 450, 455 in place over distal and proximal device portions 315, 325. One or more anatomical staples are then applied, by an anatomical stapler disposed and actuated within device 310 in e.g. a manner described with respect to previous embodiments or as otherwise known to those of ordinary skill upon reading this disclosure, to construct an anastomosis. The portion of tissue within the diameter of the staple(s) then is removed with a circular or other scalpel or other cutting device e.g. in the manner previously described herein. It should also be appreciated that pneumatic dilation of the lesion or other portion of the anatomical structure can occur prior to inserting device 310, to help ensure that adequate lumen is present to accommodate device 310 prior to insertion.

Figure 33:
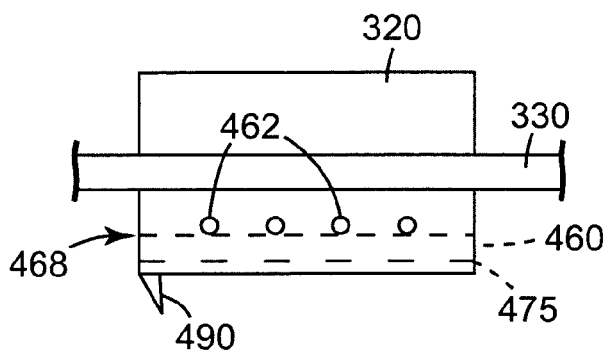
FIG. 33 is a side view according to an alternative embodiment of the invention.

Certain embodiments of the invention reduce the need for a laparoscopic procedure. According to these embodiments, device 310 is modified such that middle portion 320 of device 310 includes groove 460, as illustrated in e.g. FIGS. 33–35. Features previously described with respect to e.g. any of FIGS. 1–32 generally are equally applicable for use with respect to FIGS. 33–35, and vice versa. Groove 460 defines one or more vacuum ports 462 and is itself defined by walls 465, 470, which meet at apex 468. Row 475 of individual staples 480 extends down part or all of groove 460. Staples 480 are oriented generally perpendicularly to the mesentery or mesocolon. A driving blade or member forces staples 480 across the mesentery or mesocolon, in the manner of e.g. a GIA stapler; a handle or actuator for the driving blade extends out of device 310 via proximal portion 325. One or more anvils 485 corresponding to each staple 480 bends each staple 480 to provide hemostasis. Wall 470 provides multiple anvils having one or more appropriate grooves or depressions 485 for receiving and closing one or more ends of each staple 480. According to embodiments of the invention, all or a significant portion of row 475 of staples 480 is fired simultaneously or immediately sequentially along the length of groove 460. Additionally, middle portion 320 supports a moveable scalpel 490, other blade, electrocautery probe, or other device to be drawn along the length of groove 460 to excise tissue at or below the outer diameter of groove 460.

In use, resected portion 425 is formed, as described previously. At a point in time before, during or after formation of resected portion 425, groove 460 is positioned or repositioned on e.g. the mesenteric border 495 (FIG. 35) of the intestine, i.e. inside the intestine and generally opposite the intersection of the mesentery with the intestine. Instead of using laparoscopic techniques, vacuum source 335 applies vacuum force to groove 460 via mandrel 330 and vacuum ports 462. The vacuum force urges the mesenteric border into groove 460, such that a portion of the blood supply to the intestine is within groove 460. Note FIG. 35, for example. Row 475 of staples 480 then is fired across groove 460 to ligate the mesenteric blood supply or, in the case of another anatomical structure, other blood supply.

Figure 34:
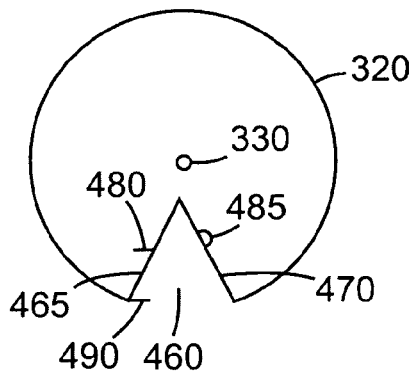
FIGS. 34–35 are end views of the FIG. 33 embodiment.
Figure 35:
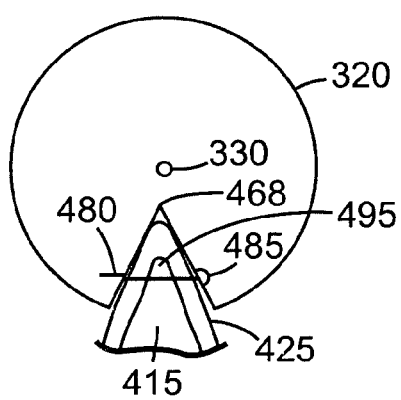

Scalpel or other device 490 then is drawn along groove 460, e.g. from one end entirely to the other end as viewed in FIG. 34, to divide the intestinal or other segment 425 from its mesentery 415. The diameter of middle portion 320 then is reduced, as described previously, and the proximal and distal ends of the intestinal or other segment are then approximated, in a manner similar to that described with respect to e.g. FIG. 32. As they are approximated, the resected segment of the intestine or other structure is withdrawn via handle or base 325.

Figure 36:
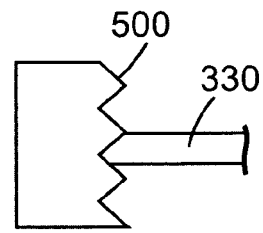
FIG. 36 is a side view according to an embodiment of the invention.
Figure 37:
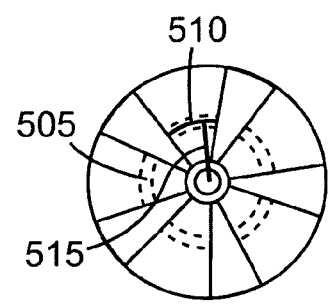
FIGS. 37–38 are end views of the FIG. 36 embodiment.
Figure 38:
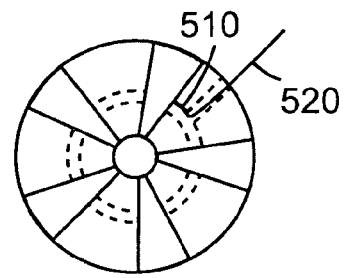

According to another embodiment of the invention illustrated in FIGS. 36–38, distal portion 315 and/or proximal portion 325 of device 310 defines crenulated, ridged, toothed or otherwise textured surface 500, such that application of vacuum pressure, as previously described, causes pleating or other texturing of the anatomical tissue held against surface 500. Features previously described with respect to e.g. FIGS. 1–35 are equally applicable for use with respect to FIGS. 36–38, and vice versa. A needle and suture, for example of wire, can then be rotated in the plane perpendicular to mandrel 330 to produce a purse string through the pleated tissue, thereby keeping the proximal and distal ends of the intestine or other anatomical structure firmly on the anastomotic device during formation of the anastomosis.

Groove 505 is formed in e.g. a rear part of distal portion 315 or proximal portion 325, as shown in FIG. 37, to accommodate curved needle 510, which has an attached suture of wire or other material. Driving arm 515 of appropriate radius rotates needle 510. A handle for arm 515 can extend through and out proximal portion 325 for manual or other actuation by a user. According to the FIG. 38 embodiment, wire 520 or other member drives curved needle 510 laparoscopically. The suture and associated tissue attached to needle 510 are removed when device 310 is withdrawn.

A further colonic anastomosis procedure according to method and device embodiments of the invention now will be described. The lesion or other diseased portion is identified by locating it endoscopically with suitable lighting, for example. Light is observed with e.g. a laparoscopic camera or other device, and a marker is placed laparoscopically. Such markers can include a tattoo or other mark of ink or other marking agent, and/or can include a mechanical device such as a suture. Device 310, which should be understood to include and/or apply to any of the other devices described or referenced herein for purposes of this description, is inserted into the colon. Device 310 or other device described herein supports a light source aimed radially outward, preferably at or about the midpoint of device 310, according to embodiments of the invention. Device 310 is inserted into the colon over an endoscope or separate from an endoscope. The light at e.g. the midpoint of device 310 is viewed laparoscopically and is positioned such that it is aligned with the marker. Harmonic scalpel or stapling device 435 is used to divide mesentery 415.

Middle portion 320 of device 310 then is expanded, as described previously, which also deploys blades 370, 375, equivalent electrocautery device(s), or like structure, using e.g. a scissors-jack type mechanism that is expanded and contracted by a screw mechanism or other threaded portion of e.g. mandrel 330. Vacuum source 335 is activated to draw normal tissue into indents 340, 345, as described previously. The tissue is cut with either blades (or equivalent) 370, 375 or scalpel/stapler 435. The diseased section of the colon is longitudinally divided and deposited into e.g. an endo catch bag, which is then removed through a laparoscopic port. Middle section 320 is reduced in diameter, blades 370, 375 retracted, and device 310 removed. Retracting mandrel 330 and middle section 320 into or toward proximal portion 325 of device 310 draws healthy distal and proximal colon portions 450, 455 into close proximity. The stapling mechanism then is fired to construct the anastomosis, e.g. in the manner previously described, and device 310 removed.

As an alternative to the endo catch bag described above, a sleeve or bag is placed over device 310, e.g. after the anastomosis is performed, to hold and carry the diseased tissue along when device 310 is removed from the intestine or other structure.

Figure 39:
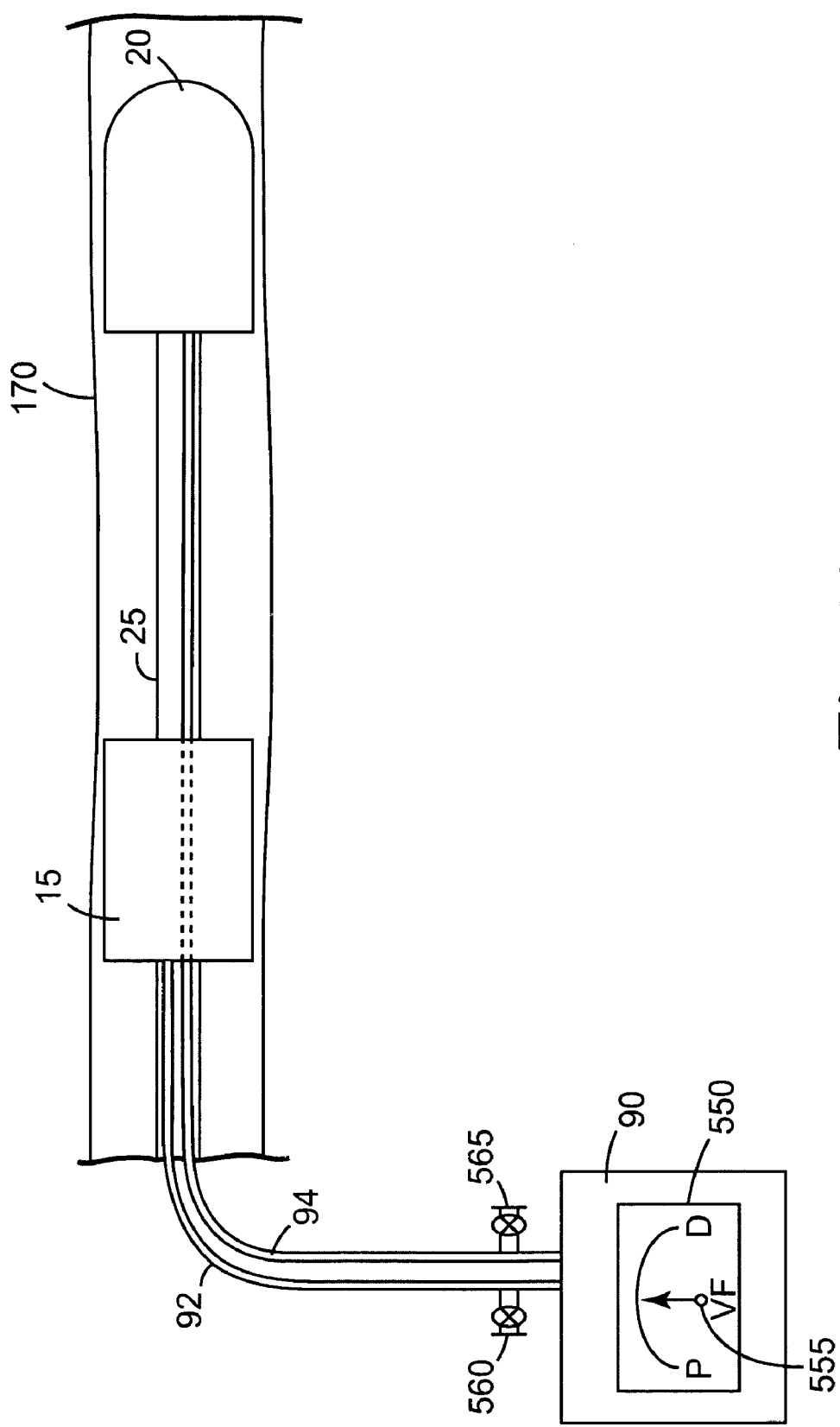
FIG. 39 shows a resection and anastomosis device with vacuum control, according to an embodiment of the invention.

Additional embodiments of the invention are described with respect to FIGS. 39–43. Features previously described with respect to FIGS. 1–38 are equally applicable for use with respect to FIGS. 39–43, and vice versa. FIG. 39 illustrates vacuum source 90, which includes or is operably associated with controller 550. Controller 550 includes control knob or equivalent feature 555, which is turned to the left toward "P" or to the right toward "D" as viewed in FIG. 39 to direct vacuum force VF more to proximal portion 15 ($VF_{proximal}$) via line or structure 92 or to distal portion 20 ($VF_{distal}$) via line or structure 94. Respective relief valves 560, 565 are provided in lines 92, 94. Alternative control features also are contemplated, for example push-button controls, linear or slider controls, keyboard controls, software controls, etc. for directing the degree of vacuum pressure to a particular portion 15, 20 and/or for controlling the total amount of pressure applied to one or both portions. Independent control of the vacuum force applied to each portion 15, 20 also is contemplated. One or more dials or other indicators are contemplated, for displaying actual (e.g. sensed, via one or more sensors associated with device 10) or directed or predicted suction force or pressure in each line/portion. Controller 550 can direct application of vacuum pressure to 100% distal, 100% proximal, or any combination or value therebetween.

Figure 40:
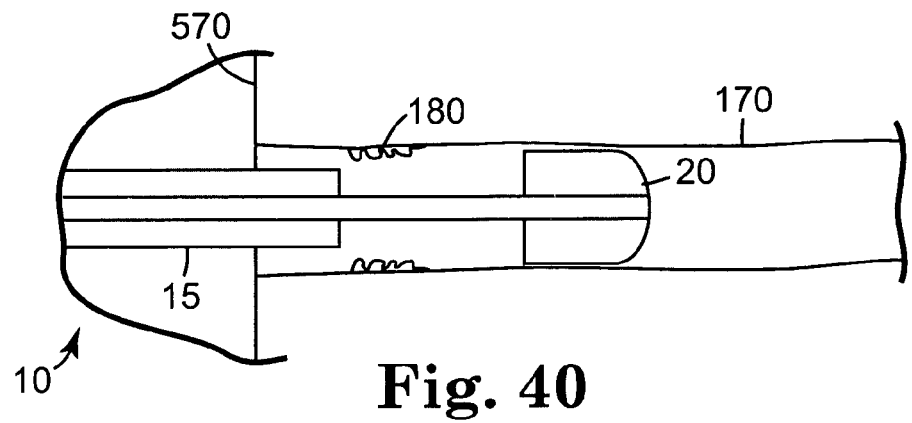
FIGS. 40–41 show a resection and anastomosis device in relation to a far-proximal lesion with respect to the device, according to an embodiment of the invention.
Figure 41:
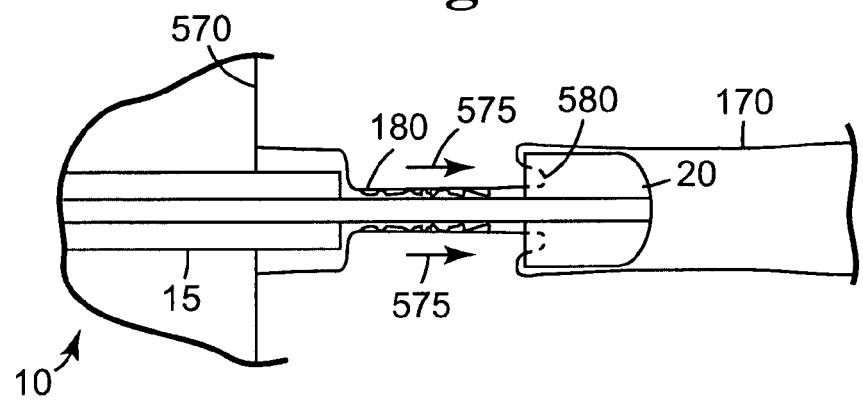
Figure 42:
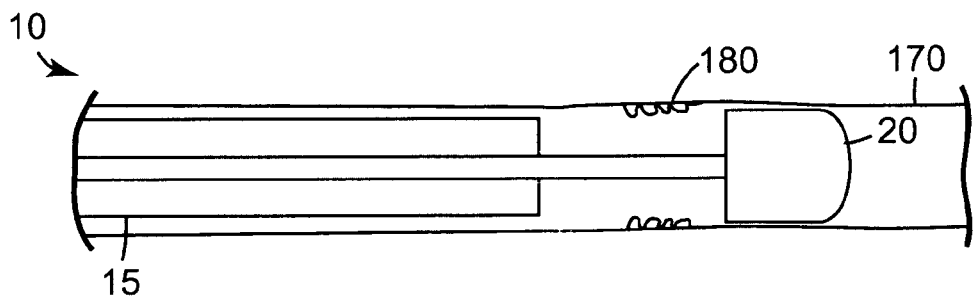
FIGS. 42–43 show a resection and anastomosis device in relation to a far-distal lesion with respect to the device, according to an embodiment of the invention.
Figure 43:
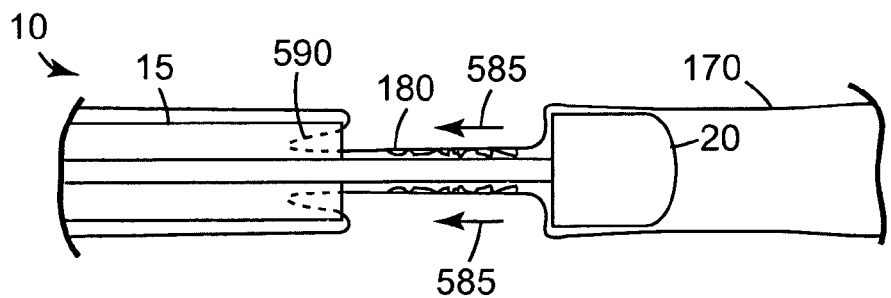

The FIG. 39 embodiment helps optimize placement of device 10 and/or a resulting anastomosis in relation to lesion 180 or other desired region of anatomical structure 170. As shown in FIG. 40, for example, lesion 180 is relatively close to rectum 570, or in a "far-proximal" position relative to device 10. In that case, vacuum pressure is controlled such that anatomical structure 170 and/or lesion 180 are drawn toward and/or collected in distal portion 20, as indicated by arrows 575 in FIG. 41. Note involuted portion 580 within distal portion 20. As another example, FIG. 42 shows lesion 180 in a "far-distal" position relative to device 10, e.g. at or near the farthest reach of device 10 within anatomical structure 170. In that case, vacuum pressure is controlled such that anatomical structure 170 and/or lesion 180 are drawn toward and/or collected in proximal portion 15, as indicated by arrows 585 in FIG. 43. Note involuted portion 590 within proximal portion 15. Thus, according to embodiments of the invention, more tissue is collected in a selected portion of device 10, or is first collected in a selected portion of device 10, in accordance with a particular surgical environment or application. Additionally, if optimal placement of device 10 is not achieved, vacuum pressure can be reduced or released so that successful re-placement can be attempted.

The embodiments of FIGS. 39–43 thus provide the ability to create far-proximal, far-distal, and central anastomoses. They also provide the ability to compensate for non-optimal placement of device 10 by varying vacuum pressure between proximal and distal portions 15, 20, and/or middle portion 25, if desired, and thus to adjust tissue-movement direction and/or speed. Reducing or releasing vacuum pressure and physically repositioning device 10 also can address non-optimal placement. The ability to vary direction and degree of vacuum force during deployment promotes optimal anastomosis formation.

According to embodiments of the invention useable in conjunction with the U.S. patent applications and U.S. patent referenced above, a helical staple with a rotating driver to engage a tang of the helical staple is located over a central rod of the device and can slide back and forth on the rod. Features previously described with respect to e.g. FIGS. 1–43 herein generally are equally applicable for use with respect to these embodiments, and vice versa. According to an associated procedure: 1) The device with a helical staple loaded onto it is inserted into the patient's colon or other anatomical structure. During insertion, the distal and proximal heads of the device are in close proximity to each other. 2) The device is inserted such that the distal head is completely past the tumor by a desired distance or is otherwise positioned. Dependent on where the lesion is in the colon, in a distal-placement configuration the distance distal to the lesion is as small as about 2 cm or less or as great as about 10 cm or greater. Endoscopic viewing through the device is possible to assist in placement. A light source is located in the device to allow visualizing location via a laparoscope, if desired. 3) The proximal portion is manually retracted such that the tumor is centered between the proximal and distal heads of the device. 4) The mesentery is located and dissected through a surgical wound, preferably laparoscopically. 5) Vacuum is applied to the distal head of the device as well as the first few cm. of the rod. The result of this vacuum is to pull the colon tissue tight to the helical stapler. 6) The helical staple is deployed by rotating the helical staple in e.g. a clockwise direction, resulting in the helical staple becoming embedded in the colon. This staple is embedded within the colon wall but does not perforate the colon outside the tissue wall. 7) With the helical staple deployed, the helical stapler is removed. 8) Alternatively to the helical staple, a constricting ring or collar, e.g. generally in the form of an automotive hose clamp, is applied laparoscopically over the distal end of the central tube on the device to secure the colon to the distal end of the device. 9) Vacuum is applied to the remainder of the rod as well as to the proximal section of the device. This pulls the colon and tumor into close proximity with the device. 10) The proximal portion of the device is expanded, thus making a larger lumen at the evacuated area and expanding the colon. 11) The distal portion of the device is retracted by pulling the rod into the proximal portion of the device. This causes the colon to involute into the distal colon and proximal portion of the device. 12) Once the distal and proximal heads of the device are in close proximity to each other, the proximal head is fully retracted so that the diameter of it is the same as the distal head. This has the result of lining up the stapler head with the anvil and the blade to the cutting groove. 13) A handle trigger is activated causing the two rows of staples to deploy as well as the cutting blade to cut the colon. 14) An annular stapling mechanism, distinct from the helical staple, is fired or otherwise actuated. 15) The vacuum is turned off and released. 16) The two heads of the device are slightly separated, allowing for separation of the stapled tissue from the device. 17) The device is withdrawn from the colon with the dissected, diseased tissue fully encapsulated within it.

Advantages provided by embodiments of the invention include the following. The procedure is done with a closed colon, generally preventing spillage of cancer cells or lumenal contents as well as generally preventing introduction of bacteria into the abdominal cavity. The surgery is less traumatic, due to e.g. the lesser number of incisions and/or the smaller surgical wound with laparoscopic guidance only. No entry by the surgeon's hands is required. Embodiments of the invention also allow access to smaller body cavities, e.g. a narrow male pelvis, when the tumor is close to the anus for example. Other advantages will be apparent to those of ordinary skill.

While the invention has been described with respect to particular embodiments, the description herein is intended to be illustrative and not necessarily limiting. For example, although specific reference has been made to treatment of the colon, embodiments of the invention are used to resect, repair, sustain and/or stabilize the colon and many other anatomical organs and structures, for example those previously referenced herein. Embodiments for use with large patients or structures are of greater length than those for use with smaller patients or structures; dimensions and materials for all embodiments are generally chosen in accordance with particular anatomies or other parameters. Embodiments of the invention are constructed for use separately and independently from a typical endoscope, for example, but also can be slid over or otherwise used with a typical endoscope. Further, movement of anatomical structure as described herein can be accomplished or assisted with suction or alternative physical maneuvering, using the disclosed apparatus, a different apparatus, or manually. As will be apparent to those of ordinary skill, the methods, structures and other features disclosed with respect to one embodiment or figure can be applied to or in combination with those of any other embodiments or figures. Various other modifications and changes will be apparent to those of ordinary skill.

What is claimed is:

1. Apparatus for moving a diseased portion of an anatomical structure with respect to a healthy portion of an anatomical structure, the apparatus comprising:
   a first vacuum section adapted to apply vacuum force to and hold the healthy portion; and
   a second vacuum section adapted to apply vacuum force to and hold the diseased portion, wherein the second vacuum section is adapted to withdraw within the first vacuum section;
   wherein the first vacuum section and the second vacuum section are adapted for placement along a longitudinal direction of the anatomical structure, further wherein the second vacuum section defines a plurality of vacuum apertures disposed relative to each other along the longitudinal direction.

2. The apparatus of claim 1, wherein the second vacuum section is adapted to draw the diseased portion into contact with the second vacuum section and to withdraw the diseased portion within the healthy portion.

3. The apparatus of claim 1, wherein the healthy portion is a first healthy portion; the apparatus further comprising a third vacuum section operably coupled with the first vacuum section and the second vacuum section, the third vacuum section being adapted to apply vacuum force to and hold a second healthy portion of the anatomical structure disposed on an opposite side of the diseased portion relative to the first healthy portion.

4. The apparatus of claim 1, further comprising a stapling device adapted to staple the anatomical structure and a cutting device adapted to cut the anatomical structure, the stapling device and the cutting device being operably coupled with the first vacuum section and the second vacuum section.

5. The apparatus of claim 1, wherein the first vacuum section and the second vacuum section are fluidly coupled with a common vacuum source.

6. The apparatus of claim 1, wherein the first vacuum section defines a first diameter and the second vacuum section defines a second diameter, the second diameter being less than about 60% of the first diameter.

7. The apparatus of claim 6, wherein the second diameter is less than about 40% of the first diameter.

8. The apparatus of claim 6, wherein the second diameter is less than about 20% of the first diameter.

9. The apparatus of claim 1, wherein the first vacuum section defines a plurality of vacuum apertures disposed relative to each other along the longitudinal direction.

10. The apparatus of claim 1, wherein the first vacuum section is adapted to hold the healthy portion against movement while the second vacuum section is withdrawn within the first vacuum section.

11. Apparatus for moving a diseased portion of an anatomical structure with respect to a healthy portion of an anatomical structure, the apparatus comprising:
   a first vacuum section adapted to apply vacuum force to and hold the healthy portion; and a second vacuum section adapted to apply vacuum force to and hold the diseased portion, wherein the second vacuum section is adapted to withdraw within the first vacuum section;

wherein the healthy portion is a first healthy portion; the apparatus further comprising a third vacuum section operably coupled with the first vacuum section and the second vacuum section, the third vacuum section being adapted to apply vacuum force to and hold a second healthy portion of the anatomical structure disposed on an opposite side of the diseased portion relative to the first healthy portion;

wherein the third vacuum section is attached to the second vacuum section for movement therewith with respect to the first vacuum section.

12. Apparatus for moving a diseased portion of an anatomical structure with respect to a healthy portion of an anatomical structure, the apparatus comprising:

a first vacuum section adapted to apply vacuum force to and hold the healthy portion; and a second vacuum section adapted to apply vacuum force to and hold the diseased portion, wherein the second vacuum section is adapted to withdraw within the first vacuum section;

wherein the healthy portion is a first healthy portion; the apparatus further comprising a third vacuum section operably coupled with the first vacuum section and the second vacuum section, the third vacuum section being adapted to apply vacuum force to and hold a second healthy portion of the anatomical structure disposed on an opposite side of the diseased portion relative to the first healthy portion;

wherein the third vacuum section comprises a cutting blade adapted to cut away the diseased portion.

13. The apparatus of claim 12, further comprising a cutting actuator for actuating the cutting blade, the cutting actuator being disposed within the second vacuum section.

14. Apparatus for moving a diseased portion of an anatomical structure with respect to a healthy portion of an anatomical structure, the apparatus comprising:

a first vacuum section adapted to apply vacuum force to and hold the healthy portion; and a second vacuum section adapted to apply vacuum force to and hold the diseased portion, wherein the second vacuum section is adapted to withdraw within the first vacuum section;

wherein the healthy portion is a first healthy portion; the apparatus further comprising a third vacuum section operably coupled with the first vacuum section and the second vacuum section, the third vacuum section being adapted to apply vacuum force to and hold a second healthy portion of the anatomical structure disposed on an opposite side of the diseased portion relative to the first healthy portion;

wherein the third vacuum section comprises a stapling device adapted to fire at least one staple into the anatomical structure.

15. The apparatus of claim 14, further comprising a stapling actuator for actuating the stapling device, the stapling actuator being disposed within the second vacuum section.

16. The apparatus of claim 14, wherein the first vacuum section defines an anvil disposed to act as a backstop for the at least one staple fired by the stapling device.

17. Apparatus for moving a diseased portion of an anatomical structure with respect to a healthy portion of an anatomical structure, the apparatus comprising:

a first vacuum section adapted to apply vacuum force to and hold the healthy portion; and a second vacuum section adapted to apply vacuum force to and hold the diseased portion, wherein the second vacuum section is adapted to withdraw within the first vacuum section;

wherein the healthy portion is a first healthy portion; the apparatus further comprising a third vacuum section operably coupled with the first vacuum section and the second vacuum section, the third vacuum section being adapted to apply vacuum force to and hold a second healthy portion of the anatomical structure disposed on an opposite side of the diseased portion relative to the first healthy portion;

wherein the third vacuum section comprises an internal wall, the second vacuum section being supported by the internal wall.

18. The apparatus of claim 17, wherein the internal wall defines vacuum apertures therethrough, the vacuum apertures being adapted to transmit vacuum force in the second vacuum section through the internal wall.

19. Apparatus for moving a diseased portion of an anatomical structure with respect to a healthy portion of an anatomical structure, the apparatus comprising:

a first vacuum section adapted to apply vacuum force to and hold the healthy portion; and a second vacuum section adapted to apply vacuum force to and hold the diseased portion, wherein the second vacuum section is adapted to withdraw within the first vacuum section;

wherein the first vacuum section is adapted to expand and contract with respect to the anatomical structure.

20. Apparatus for moving a diseased portion of an anatomical structure with respect to a healthy portion of an anatomical structure, the apparatus comprising:

a first vacuum section adapted to apply vacuum force to and hold the healthy portion;

a second vacuum section adapted to apply vacuum force to and hold the diseased portion, wherein the second vacuum section is adapted to withdraw within the first vacuum section;

a stapling device adapted to staple the anatomical structure and a cutting device adapted to cut the anatomical structure, the stapling device and the cutting device being operably coupled with the first vacuum section and the second vacuum section; and a support adapted for movement with the second vacuum section with respect to the first vacuum section, the support holding one or both of the stapling device and the cutting device.

21. Apparatus for moving a diseased portion of an anatomical structure with respect to a healthy portion of an anatomical structure, the apparatus comprising:

a first vacuum section adapted to apply vacuum force to and hold the healthy portion; and a second vacuum section adapted to apply vacuum force to and hold the diseased portion, wherein the second vacuum section is adapted to withdraw within the first vacuum section;

wherein the first vacuum section and the second vacuum section are fluidly coupled with a common vacuum source; and wherein the vacuum source is adapted to create a vacuum force within the first vacuum section, further wherein the apparatus is adapted to transmit the vacuum force from the first vacuum section to the second vacuum section.

22. Resection apparatus for use with anatomical tissue, the apparatus comprising:
 a proximal portion;
 a distal portion operably coupled with the proximal portion;
 an intermediate portion operably coupled with the proximal portion and the distal portion, the intermediate portion being adapted for movement within the proximal portion, the intermediate portion further being adapted to apply suction to attract anatomical tissue;
 a cutting device adapted to cut anatomical tissue, the cutting device being supported by either the proximal portion or the distal portion; and
 a stapling device adapted to staple anatomical tissue, the stapling device being supported by either the proximal portion or the distal portion;
 wherein at least one of the proximal portion and the distal portion are adapted to apply suction to attract anatomical tissue;
 wherein both the proximal portion and the distal portion are adapted to apply suction to attract anatomical tissue.

23. The apparatus of claim 22, wherein the intermediate portion supports the distal portion for movement therewith.

24. The apparatus of claim 23, wherein the distal portion comprises an internal support adapted to receive the intermediate portion; further wherein the distal portion is adapted to apply suction on opposite sides of the internal support to attract anatomical tissue.

25. The apparatus of claim 22, wherein the proximal portion comprises an O-ring for providing a fluid seal relative to the intermediate portion.

26. The apparatus of claim 22, further comprising one or more collars adapted to hold the anatomical tissue with respect to the intermediate portion.

27. The apparatus of claim 26, wherein the one or more collars are adapted to move within the proximal portion as the intermediate portion moves within the proximal portion.

28. Device for moving anatomical tissue, the device comprising:
 a proximal portion defining an interior adapted to receive involuted anatomical tissue;
 a distal portion operably coupled with the proximal portion, the distal portion being supported for movement with respect to the proximal portion, the distal portion defining an interior adapted to receive involuted anatomical tissue; and
 movement structure adapted to move anatomical tissue into the interior of the proximal portion and into the interior of the distal portion, the movement structure also being adapted to cause involution of the anatomical tissue in the interior of the proximal portion and in the interior of the distal portion;
 wherein the proximal portion and the distal portion are adapted to be disconnected; further wherein the proximal portion comprises structure for receiving the distal portion such that connection of the distal portion to the proximal portion initiates or allows involution of the anatomical tissue into the distal portion.

29. The device of claim 28, wherein the movement structure comprises vacuum apertures defined in the proximal portion and in the distal portion, the vacuum apertures being directed to the interior of the proximal portion and to the interior of the distal portion, respectively, the vacuum apertures being fluidly coupled with at least one vacuum source.

30. The device of claim 28, further comprising a fastening device, supported by one of the proximal portion and the distal portion, for fastening anatomical tissue.

31. The device of claim 30, further comprising a cutting device, supported by one of the proximal portion and the distal portion, for cutting the involuted anatomical tissue.

32. The device of claim 28, wherein the volume of the interior of the distal portion into which anatomical tissue can be moved is different than the volume of the interior of the proximal portion into which anatomical tissue can be moved.

33. Device for moving anatomical tissue, the device comprising:
 a proximal portion defining an interior adapted to receive involuted anatomical tissue;
 a distal portion operably coupled with the proximal portion, the distal portion being supported for movement with respect to the proximal portion, the distal portion defining an interior adapted to receive involuted anatomical tissue; and
 movement structure adapted to move anatomical tissue into the interior of the proximal portion and into the interior of the distal portion, the movement structure also being adapted to cause involution of the anatomical tissue in the interior of the proximal portion and in the interior of the distal portion;
 wherein the movement structure comprises vacuum apertures defined in the proximal portion and in the distal portion, the vacuum apertures being directed to the interior of the proximal portion and to the interior of the distal portion, respectively, the vacuum apertures being fluidly coupled with at least one vacuum source;
 wherein the vacuum apertures are directed to both the interior and the exterior of the proximal portion and the distal portion.

34. Device for moving anatomical tissue, the device comprising:
 a proximal portion defining an interior adapted to receive involuted anatomical tissue;
 a distal portion operably coupled with the proximal portion, the distal portion being supported for movement with respect to the proximal portion, the distal portion defining an interior adapted to receive involuted anatomical tissue; and
 movement structure adapted to move anatomical tissue into the interior of the proximal portion and into the interior of the distal portion, the movement structure also being adapted to cause involution of the anatomical tissue in the interior of the proximal portion and in the interior of the distal portion;
 wherein the movement structure comprises at least one vacuum source and defines vacuum apertures fluidly coupled with the vacuum source, the vacuum apertures being defined in at least one of the proximal portion and distal portion; further wherein the movement structure defines a longitudinal opening in said at least one portion through which anatomical tissue moves into the interior of said at least one portion; further wherein a total cross-sectional area defined by the vacuum apertures of said at least one portion exceeds a total cross-sectional area of the longitudinal opening defined by said at least one portion such that total vacuum force per unit area applied to the tissue by said at least one portion is sufficient to hold anatomical tissue against the outer circumference of said at least one portion without allowing that anatomical tissue to be pulled into said at least one portion as tissue involution occurs.

35. Device for moving anatomical tissue, the device comprising:
    a proximal portion defining an interior adapted to receive involuted anatomical tissue;
    a distal portion operably coupled with the proximal portion, the distal portion being supported for movement with respect to the proximal portion, the distal portion defining an interior adapted to receive involuted anatomical tissue; and
    movement structure adapted to move anatomical tissue into the interior of the proximal portion and into the interior of the distal portion, the movement structure also being adapted to cause involution of the anatomical tissue in the interior of the proximal portion and in the interior of the distal portion;
    wherein the movement structure comprises at least one vacuum source fluidly coupled with the proximal portion and the distal portion for applying vacuum force; further wherein the amount of vacuum force applied to the proximal portion and to the distal portion can be controlled individually.

36. The device of claim 35, wherein the movement structure comprises a control knob operably coupled with the vacuum source to individually control the amount of vacuum force applied to the proximal portion and to the distal portion.

37. Apparatus for insertion into anatomical tissue, the apparatus comprising:
    a proximal portion;
    a distal portion adapted for movement relative to the proximal portion;
    at least one vacuum source fluidly coupled with the proximal portion and the distal portion, the at least one vacuum source being adapted to apply vacuum force to the proximal portion and the distal portion to draw anatomical tissue toward the proximal portion and distal portion, respectively; and
    a controller operably coupled with the at least one vacuum source to adjust the balance of vacuum force applied by the at least one vacuum source between the proximal portion and the distal portion, to favor anatomical tissue movement toward either the proximal portion or distal portion.

38. The apparatus of claim 37, wherein both the proximal portion and the distal portion are adapted to receive involuted anatomical tissue therewithin in response to the application of vacuum force.

39. A method of holding anatomical structure, comprising:
    inserting a first holding device into anatomical structure to be held;
    involuting the anatomical structure within the first holding device by applying vacuum to the anatomical structure through the first holding device such that the first holding device holds the anatomical structure;
    connecting a disconnected second holding device to the first holding device, the second holding device being adapted to hold the anatomical structure;
    applying vacuum to the second holding device via the first holding device;
    involuting the anatomical structure within the second holding device; and
    moving the first holding device and the second holding device toward each other to join the anatomical structure held by the first holding device with the anatomical structure held by the second holding device.

40. The method of claim 39, further comprising tying the anatomical structure to the second holding device before the moving.

* * * * *